(12) United States Patent
Yu

(10) Patent No.: US 10,858,383 B2
(45) Date of Patent: Dec. 8, 2020

(54) REMOTE HETEROARYL ALKENYLATION WITH CATALYTIC BIFUNCTIONAL TEMPLATE

(71) Applicant: The Scripps Research Institute, La Jolla, CA (US)

(72) Inventor: Jin-Quan Yu, San Diego, CA (US)

(73) Assignee: The Scripps Research Institute, La Jolla, CA (US)

(*) Notice: Subject to any disclaimer, the term of this patent is extended or adjusted under 35 U.S.C. 154(b) by 0 days.

(21) Appl. No.: 16/485,931

(22) PCT Filed: Feb. 13, 2018

(86) PCT No.: PCT/US2018/018000
§ 371 (c)(1),
(2) Date: Aug. 14, 2019

(87) PCT Pub. No.: WO2018/152107
PCT Pub. Date: Aug. 23, 2018

(65) Prior Publication Data
US 2020/0131213 A1    Apr. 30, 2020

Related U.S. Application Data

(60) Provisional application No. 62/458,750, filed on Feb. 14, 2017.

(51) Int. Cl.
*C07F 15/00* (2006.01)
*C07D 213/04* (2006.01)
*C07D 215/06* (2006.01)

(52) U.S. Cl.
CPC ........ *C07F 15/0093* (2013.01); *C07D 213/04* (2013.01); *C07D 215/06* (2013.01)

(58) Field of Classification Search
None
See application file for complete search history.

(56) References Cited

PUBLICATIONS

Chu et al. Remote Meta-C—H Activation Using a Pyridine-Based Template: Achieving Site-Selectivity via the Recognition of Distance and Geometry. ACS Central Science, vol. 1, Oct. 16, 2015, 394-399.*

* cited by examiner

*Primary Examiner* — Clinton A Brooks
(74) *Attorney, Agent, or Firm* — Geoffrey K. Cooper; Hugh Wang

(57) ABSTRACT

We report the design of a catalytic, bifunctional template that binds heterocyclic substrate via reversible coordination instead of covalent linkage, allowing remote site-selective C—H olefination of heterocycles. The two metal centers coordinated to this template play different roles; anchoring substrates to the proximity of catalyst and cleaving the remote C—H bonds respectively. Using this strategy, we demonstrate remote site-selective C—H olefination of heterocyclic substrates which do not have functional group handles for covalently attaching templates. For instance the olefination can be an alkenylation of a 3-phenylpyridine with an acrylate alkyl ester selective for the meta position of the phenyl group with respect to the pyridine, or can be an alkenylation of a quinoline with an acrylate alkyl ester selective for the 5-position of the quinoline.

10 Claims, 4 Drawing Sheets

REMOTE HETEROARYL ALKENYLATION WITH CATALYTIC BIFUNCTIONAL TEMPLATE

CROSS-REFERENCE TO RELATED APPLICATION

This application claims the priority of U.S. provisional application Ser. No. 62/458,750, filed Feb. 14, 2017, the disclosure of which is incorporated herein by reference in its entirety.

STATEMENT OF GOVERNMENT SUPPORT

This invention was made with government support under 1R01 GM102265 awarded by the National Institutes of Health. The government has certain rights in the invention.

BACKGROUND

Converting C—H bonds directly into carbon-carbon and carbon-heteroatom bonds can significantly improve step-economy in synthesis by providing alternative disconnections to traditional functional group manipulations. In this context, directed C—H activation reactions have been extensively explored for regioselective functionalization[1-5]. Though applicability can be severely curtailed by distance from the directing group and the shape of the molecule, a number of approaches have been developed to overcome this limitation[6-12]. For instance, recognition of the distal and geometric relationship between an existing functional group and multiple C—H bonds has recently been exploited to achieve meta-selective C—H activation by use of a covalently attached U-shaped template[13-17]. However, stoichiometric installation of the template is not feasible in the absence of an appropriate functional group handle.

We recently developed U-shaped templates that accommodate a macrocyclic cyclophane transition state[13], thereby allowing the activation of meta-C—H bonds (FIG. 1). Despite substantial improvements in the scope and efficiency of this approach, the need for an appropriate functional group handle to covalently attach the stoichiometric template is a limitation. A large number of medicinally important heterocycles are not compatible with our template approach because there are no methods to covalently tether the template to the heterocycle. A prominent example is 3-phenylpyridine motif 1a which is found in more than 6,600 bioactive compounds including a number of pharmaceutical agents according to the PubChem database (FIG. 1a). Coordination of a metal catalyst with the pyridyl nitrogen in these heterocycles typically prohibits transition metal catalysts from reaching distal C—H bonds in these substrates. We wondered whether such reliable non-productive coordination can be harnessed to assemble pre-transition state for C—H activation in supramolecular fashion. A reversible hydrogen bond has recently been employed to anchor an iridium catalyst with appropriate distance and geometry to significantly improve the meta-selectivity in the C—H borylation of benzamides from 66:34 to 96:4 (m:p ratio)[18]. The high reactivity of the Ir-catalyzed C—H borylation in the absence of directing effect was crucial for this success. Thus far, the exploitation of the hydrogen bonding approach to achieve Pd-catalyzed remote meta-selective C—H activation has not been successful due to lack of reactivity.

SUMMARY

The invention provides, in various embodiments, a palladium-coordinating template compound for directing alkenylation of a heteroaryl, the template compound of formula (I)

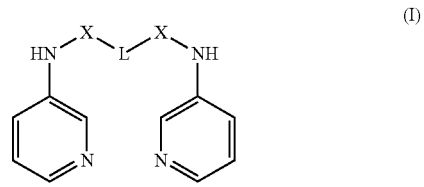

wherein X is C=O or $SO_2$, and L is a 2-3 carbon alkylene linker which can be substituted with one or more alkyl groups or can be included in a cycloalkyl ring which can be substituted with one or more alkyl or can be unsubstituted. For example, for the template compound of formula (I), X can be $SO_2$; or L can be one of an ethylene or a 1,1,2,2,-tetramethylethylene linker or can be a two-carbon moiety comprised by a cyclohexyl ring; or both.

Further, the invention can provide a method of carrying out an alkenylation of a heteroaryl compound comprising a 3-phenylpyridine group having a hydrogen atom disposed on the phenyl ring meta to the point of attachment to the pyridine ring, comprising contacting the compound comprising the 3-phenypyridine group and an acrylate alkyl ester having at least one acrylate β-hydrogen, in the presence of the template compound of formula (I), an N-acylaminoacid, a Pd(II) salt, an Ag(I) salt, and a Cu(II) salt, in a solvent milieu comprising 1,1,1,3,3,3-hexafluoro-2-propanol (HFIP). For example, the method can employ for the template compound of formula (I), a template compound wherein X is $SO_2$, or L is an ethylene, or L is a 1,1,2,2,-tetramethylethylene linker, or any combination thereof. More specifically, the N-acylaminoacid can be N-acetylglycine. More specifically, the Pd(II) salt can be $Pd(OAc)_2$, the Ag(I) salt can be $AgBF_4$, the Cu(II) salt can be $Cu(OAc)_2$, and the method can be carried out in the presence of air or oxygen. More specifically, the acrylate alkyl ester can be ethyl acrylate.

In various embodiments of the method, the 3-phenylpyridine group cab have a hydrogen atom disposed on the phenyl ring meta to the point of attachment to the pyridine ring and also have a hydrogen atom disposed on the phenyl ring ortho to the point of attachment, or a hydrogen atom disposed para to the point of attachment, or both, wherein the alkenylation reaction is selective for the substitution of the meta position.

More specifically, the template compound can be of formula T1

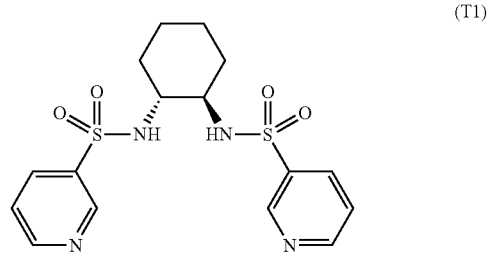 [SMILES: O=S(=O)(N[C@@H]1CCCC[C@H]1NS(=O)(=O)c1cccnc1)c1cccnc1]

or T8

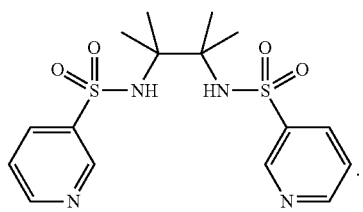

(T8)

The invention can further provide, in various embodiments, a palladium-coordinating template compound for directing alkenylation of a heteroaryl, the template compound of formula (II)

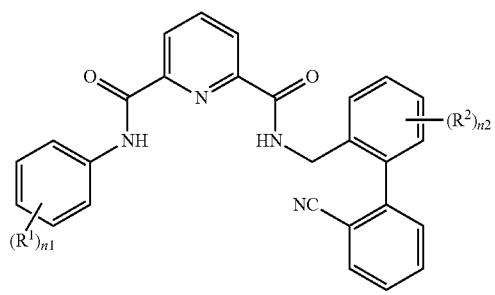

(II)

wherein each independently selected $R^1$ is halo, trifluoromethyl, (C1-C4)alkyl, or (C1-C4)alkoxy, and n1 is 0, 1, 2, or 3; and, each independently selected $R^2$ is halo, trifluoromethyl, (C1-C4)alkyl, or (C1-C4)alkoxy, and n1 is 0, 1, 2, or 3.

The invention further provides a template palladium complex of formula (III), for use in carrying out methods of the invention. The template palladium complex comprises per molecule of the template compound of formula (II), an atom of Pd(II), and a molecule of acetonitrile.

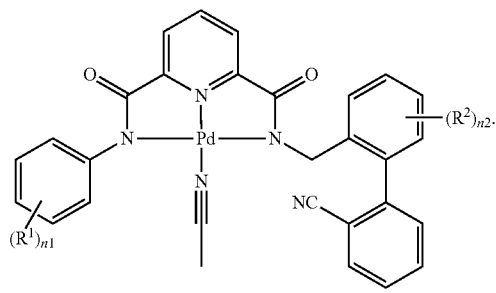

(III)

More specifically, for the template palladium complex of formula (III), $R^1$ can be independently selected trifluoromethyl, t-butyl, or methoxy, and $R^2$ can be independently selected fluoro, ethyl, or t-butyl, or any combination thereof.

The invention further provides a method of preparation of a template palladium complex of formula (III), comprising contacting a template compound of formula (II), a Pd(II) compound, and acetonitrile.

The invention further provides, in various embodiments, a method of carrying out an alkenylation of a compound comprising a quinoline group having a hydrogen atom disposed on the 5-position thereof, comprising contacting the compound comprising the quinoline group and an acrylate ester having at least one 1-hydrogen, in the presence of a pre-assembled template palladium complex of formula (III), an N-acylaminoacid, a Pd(II) salt, an Ag(I) salt, and a Cu(II) salt, in a solvent milieu comprising 1,1,1,3,3,3-hexafluoro-2-propanol (HFIP). More specifically, the N-acylaminoacid can be N-acetylglycine. More specifically, the Pd(II) salt can be Pd(OAc)$_2$, the Ag(I) salt can be AgBF$_4$, the Cu(II) salt can be Cu(OAc)$_2$, or any combination thereof; and wherein the method can be carried out in the presence of air or oxygen. More specifically, the acrylate alkyl ester can be ethyl acrylate.

In various embodiments of the method, the compound comprising a quinoline group having a hydrogen atom disposed on the 5-position thereof has further hydrogen substitution on other positions of the quinoline, and the alkenylation reaction of the present inventive method is selective for the 5-position of the quinoline.

In various embodiments of the method, the pre-assembled template palladium complex of formula (III) can be of any one of formula T15

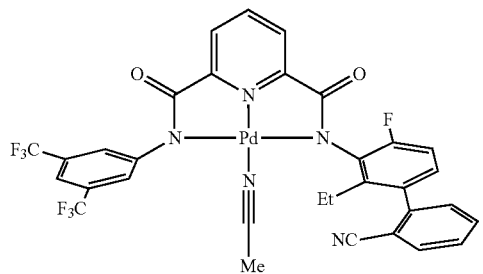

(T15)

T16

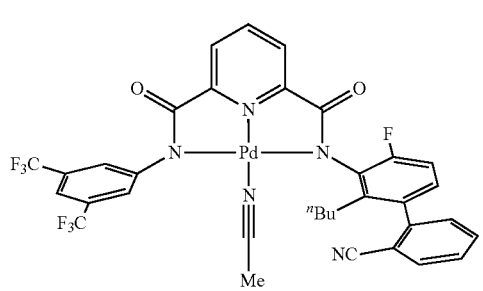

(T16)

T17

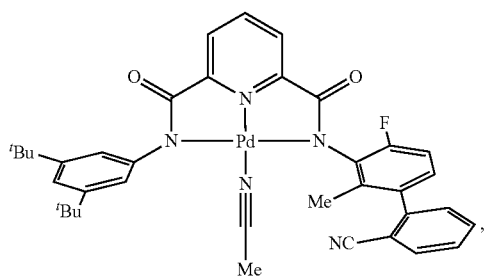

(T17)

or T18

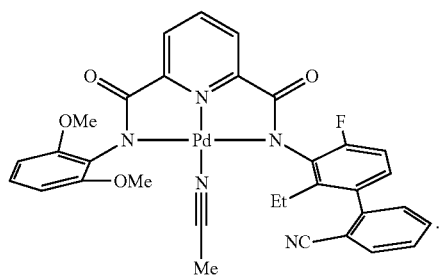

(T18)

In various embodiments of the method, the N-acylamino-acid is N-acetylglycine, the Pd(II) salt is Pd(OAc)$_2$, the Ag(I) salt is AgBF$_4$, the Cu(II) salt is Cu(OAc)$_2$, the acrylate alkyl ester is ethyl acrylate, and the method is carried out in the presence of air or oxygen.

DETAILED DESCRIPTION

Figure 1:
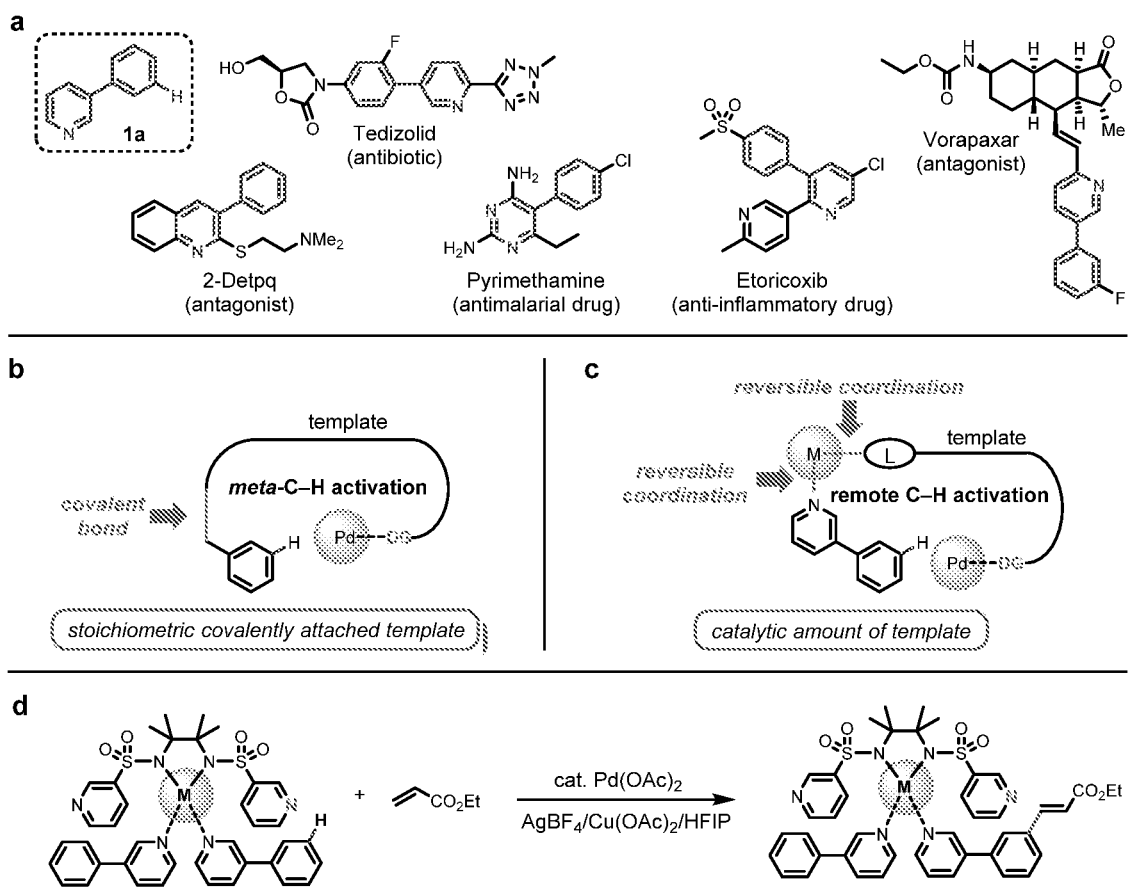
FIG. 1|Design of a cooperative bimetallic approach for remote site-selective C—H activation. a, Model substrate 1a and structurally related pharmaceutical agents. b, Previously developed covalently attached U-shaped template strategy for meta-C—H activation. c, The bimetallic strategy for remote site-selective C—H activation. d, Remote site-selective C—H olefination. DG, directing group; M, metal ion; L, coordinating moieties. HFIP: hexafluoroisopropanol.
Figure 2:
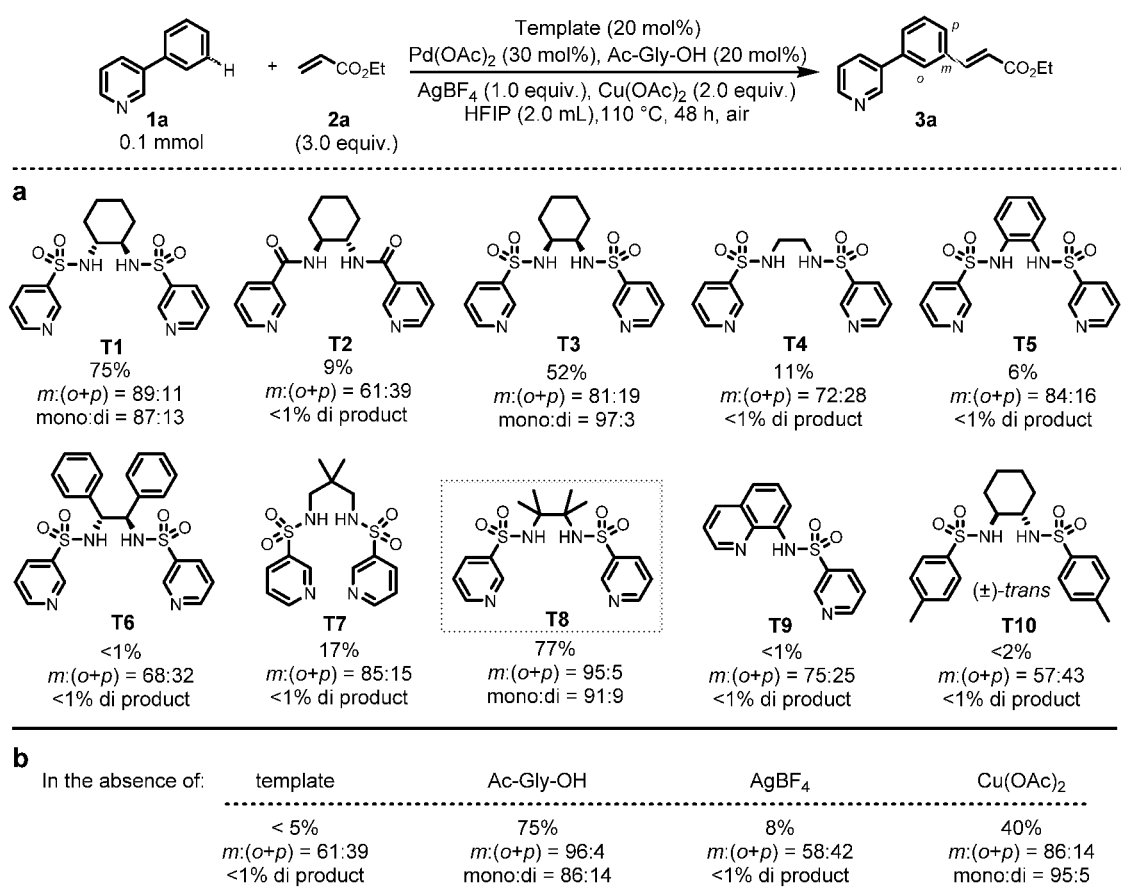
FIG. 2|Discovery of a template that enables site-selective remote C—H activation. a, Template evaluation. b, Control experiments with T8 as template. The yield (percentage under each structure) of the olefinated products, the meta:(ortho+para) ratio of mono-olefinated products and ratio of mono- and di-olefinated products (mono:di) were determined by $^1$H NMR analysis of the unpurified reaction mixture using CH$_2$Br$_2$ as the internal standard (assisted with GOC-MS analysis), the variance is estimated to be within 5%. Ac-Gly-OH: N-acetyl-glycine.

To achieve both the reactivity and meta-selectivity observed using the covalent template approach[13], we envision the covalent linkage could be replaced by a reversible metal coordination as shown in FIG. 1b. In essence, the often undesired coordination of heterocycles with metal centers is utilized to anchor the substrates to the template reversibly. Following this key design principle, a bifunctional template coordinated with two metal centers[19-22] simultaneously is devised to play dual roles: (A) the bis-amide backbone chelates with a metal center that can recruit the substrate via binding to the heterocycles; (B) directing groups on the side arm will direct the palladium catalyst to the specific remote C—H bonds (FIG. 1d). We chose a bis-amide T1 as the backbone for attaching the U-shaped templates due to their ability to chelate with Pd(II) or Cu(II) centers[23-24] which will be present in our reaction. Since we have recently demonstrated that a properly positioned C-3 pyridyl group could also function as a U-shaped template in a meta-selective iodination reaction[13,17] we choose C-3 pyridine over the nitrile directing group to enhance the coordination with the small amount of Pd(II) catalyst. With these considerations in mind, we synthesized various templates based on the bis-sulfonamide and bis-amide scaffolds containing the directing C-3 pyridine group as pendant side arms. The pyridyl nitrogen atom is positioned at C-3 instead of C-2 to avoid the formation of bisdendate chelation with the sulfonamide or amide. We evaluated these templates using olefination of 1a as the model reaction (FIG. 2). Under the optimized conditions, olefination of 1a in the presence of 20 mol % template and 30 mol % Pd(OAc)$_2$ gave olefinated products in 75% total yield. Importantly, synthetically useful remote meta-selectivity was obtained (meta:(ortho+para)= 89:11). Replacement of the sulfonamide moieties in T1 with carboxamides (T2) resulted in dramatic decrease in both yield (9%) and m:(o+p) ratio (61:39). Switching from a trans to cis-cyclohexane backbone (T3) also reduced the yield significantly (52%). Although the less rigid acyclic ethylenediamine backbones were not effective (T4-T7), template T8 derived from the sterically hindered 2,3-dimethyl-2,3-butanediamine was found to be the most effective, affording the olefination products in 77% yield and excellent meta-selectivity (95:5). These experimental results indicate the importance of the conformational constrain of the backbone which is consistent with the notion that reactivity and selectivity in remote C—H activation is based on precise recognition of distance and geometry. Notably, mono-selectivity obtained using this bimetallic approach is significantly higher than the previously reported meta-C—H olefinations using covalently attached templates[3-15]. Presumably, the mono-olefinated product is significantly less reactive due to steric hindrance as the bimetallic assembly is highly sensitive to conformational changes. Replacing T8 with a simplified scaffold (T9) led to loss of reactivity. Template T10 bearing tolyl substituents instead of the C-3 pyridyl groups on the side arm gave 2% of the mono-olefinated products with poor meta-selectivity (m:(o+p)=57:43), confirming the remote directing effect of this bifunctional template.

To elucidate the roles of the key components of this reaction, a number of control experiments have been carried out (FIG. 2b). In the absence of T8, the olefination reaction gave less than 5% of the mono-olefinated products with low m:(o+p) ratio (61:39) indicating the essential directing effect from the template. Notably, this remote directing effect controls the site-selectivity based on distance and geometry, which is fundamentally different from previously observed C-2 or C-4 selectivity of pyridines that are governed by electronic and steric effects amplified by the presence of a Lewis acidic metal[25,26]. The nearly complete loss of reactivity and meta-selectivity by removing the silver salts from the reaction is intriguing, although the formation of a Pd—Ag heterodimer in the transition state could potentially account for this phenomenon[27]. Notably, other silver salts are less effective (see Supplementary Information). We anticipate both Cu(II) and Pd(II) could coordinate with the bis-amide scaffold and impact this reaction. Indeed, both the yield and meta-selectivity decreased significantly in the absence of Cu(OAc)$_2$. Removal of N-acetyl-protected glycine (Ac-Gly-OH) ligand from the standard conditions only decreased the mono-selectivity, presumably due the steric effect.

Figure 3:
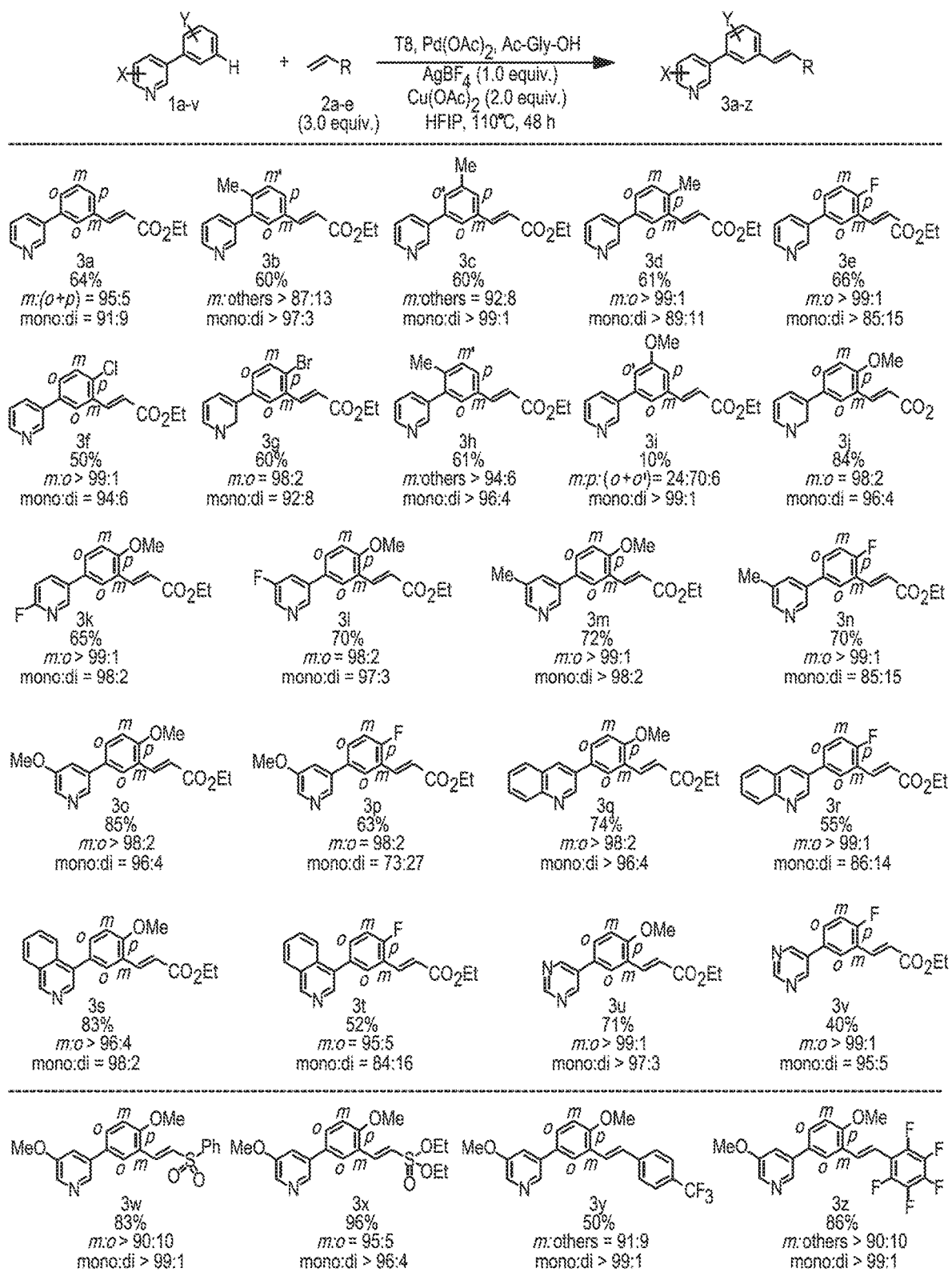
FIG. 3|Remote site-selective C—H olefination of heterocycle-containing substrates using a catalytic template. The percentages under each structure indicate isolated yields of the mono-olefinated meta product. The meta-selectivity of mono-olefinated products and ratio of mono- and di-olefinated products were determined by $^1$H NMR analysis of the unpurified reaction mixture (assisted with GOC-MS analysis), the variance is estimated to be within 5%. Reaction conditions (unless otherwise noted): 1a-v (0.1 mmol), T8 (20 mol %), Pd(OAc)$_2$ (30 mol %), Ac-Gly-OH (20 mol %), AgBF$_4$ (1.0 equiv.), Cu(OAc)$_2$ (2.0 equiv.), 2a-e (3.0 equiv.), HFIP (2.0 mL), 110° C., 48 h. For 3h-m, 3o, 3q, 3s, 3u, 3w and 3z: T8 (15 mol %), Pd(OAc)$_2$ (20 mol %), Ac-Gly-OH (5 mol %). For 3p, 3t, 3v and 3y: 130° C. For 3h-j and 3x: 72 h. For 3k, 3q and 3s: 24 h.

Next, we applied template T8 to the remote meta-selective C—H olefination of 3-phenylpyridine derivatives (FIG. 3). The mono-meta-olefinated 3-phenylpyridine 3a was obtained in 65% isolated yield. Methyl substituents on the ortho, meta and para positions of the phenyl ring were tolerated providing similar yields and mono-selectivity (3b-d). Substrates containing fluorine, chlorine and bromine substituents on the para position of the phenyl ring are olefinated to give the meta-product in 50-66% yields with excellent meta-selectivity and good mono-selectivity (3e-g). An ortho-methoxy group was also tolerated, providing 61% yield and excellent meta-selectivity and mono-selectivity (3h). A meta-methoxy group reduced the yield of isolated meta-olefination product to 10% with a complete loss of meta-selectivity (3i). In general, the meta-substitution in substrates interfered with the optimum conformational orientation due to steric effects, consistent with the observed excellent mono-selectivity in contrast to previous meta-selective C—H activation reactions[13-15]. Para-methoxy substituted substrate gave excellent yield, meta-selectivity and mono-selectivity. Various substituents on the pyridine ring were also examined. Both C-2 and C-3 fluorine on the pyridine ring were well tolerated, providing 65% and 70% yield of the desired products respectively with excellent meta-mono-selectivity (3k, 3l). Electron-donating methyl and methoxy groups on the 3-position of the pyridine ring afforded the desired meta-products in 63-85% yields with excellent meta-selectivity (3m-p). To further explore the scope of this methodology, substrates containing quinoline and isoquinoline were also olefinated to give the meta-products in moderate to good yields (52-83%) and good selectivity (3q-t). 5-phenylpyrimidine substrates, another pharmaceutically important heterocycle family[28,29], was also tolerated (3u, 3v). In expanding the scope of the olefin coupling partners, unsaturated sulfone and phosphonate are reactive, giving good to excellent yields with excellent meta- and mono-selectivity (3w, 3x). Meta-olefination with electron-deficient styrene was also demonstrated (3y, 3z). To investigate whether the template can be recovered, olefination of 1o was also performed on 1 gram scale to give 3o in 70% yield (m:o=99:1, mono:di=98:2). The template is readily recovered in 96% by chromatography.

Figure 4:
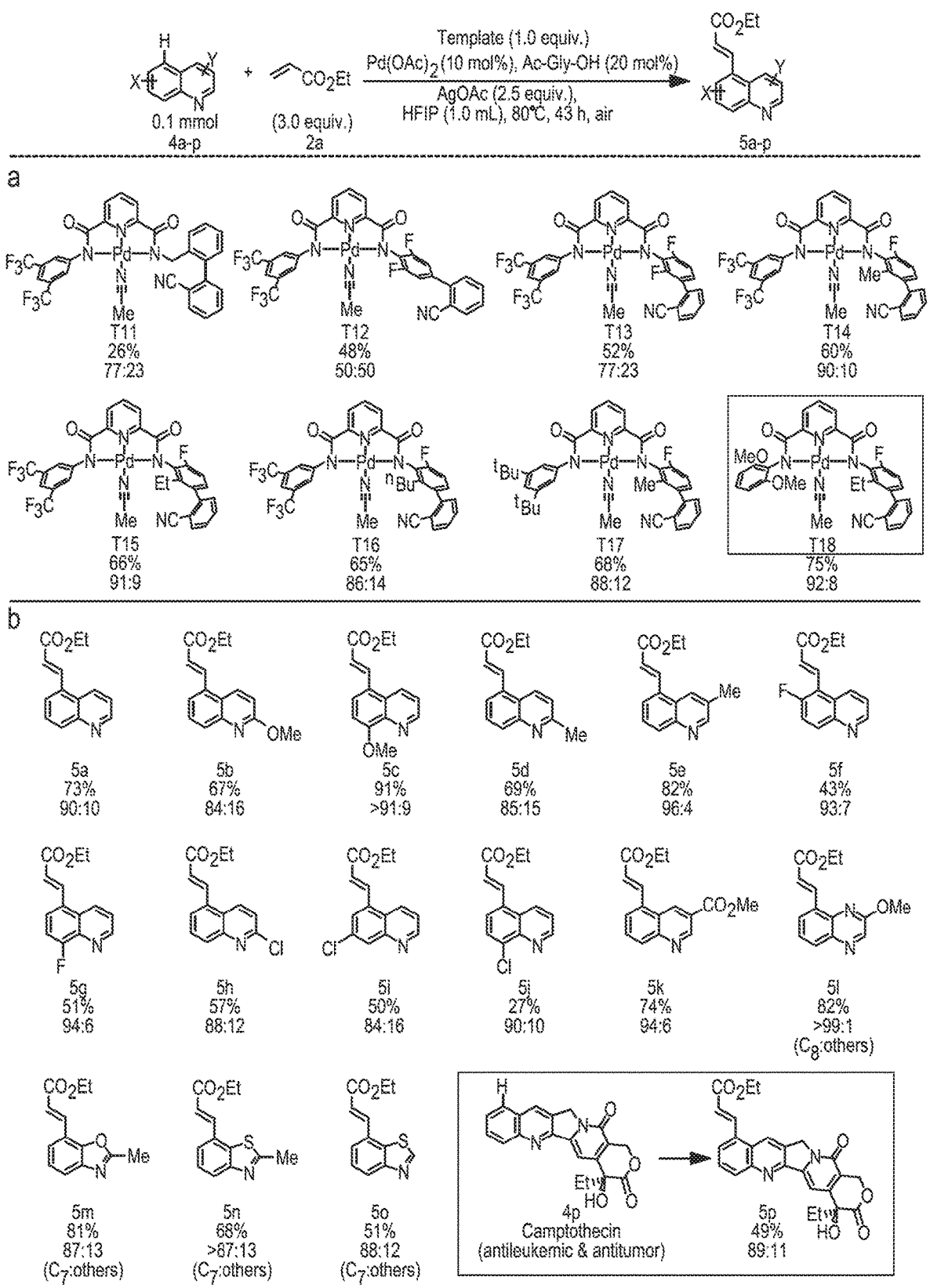
FIG. 4|Remote site-selective C—H olefination of heterocycles using a non-covalent template. a, Template evaluation. b, Substrate scope. The percentages under each structure indicate the yields of the isolated olefinated products (unless otherwise noted). The ratio of the major product to other isomers (C$_5$:others, unless otherwise noted) were determined by $^1$H NMR analysis of the unpurified reaction mixture (assisted with GC-MS analysis), the variance is estimated to be within 5%. For template evaluation (a): The yields were determined by $^1$H NMR analysis of the unpurified reaction mixture using 1,3,5-trimethoxybenzene as the internal standard. Reaction conditions for template evaluation (a): 4a (0.1 mmol), template (1.0 equiv.), Pd(OAc)$_2$ (15 mol %), Ac-Gly-OH (20 mol %), AgOAc (2.0 equiv.), 2a (3.0 equiv.), HFIP (1.0 mL), 100° C., 12 h. Reaction conditions for substrate scope (b), (unless otherwise noted): substrates (0.1 mmol), T18 (1.0 equiv.), Pd(OAc)$_2$ (10 mol %), Ac-Gly-OH (20 mol %), AgOAc (2.5 equiv.), 2a (3.0 equiv.), HFIP (1.0 mL), 80° C., 43 h. For 5b, 5d, 5h and 5p: T14 was used as template. For 5k and 5l: 22 h. For 5m: 20 h. For 5p: 48 h, AgOAc (5.0 equiv.).

To test the feasibility of extending the design principle of this bimetallic catalysis to different classes of heterocycles, we embarked on site-selective C—H olefination of quinolines which are ubiquitous in drug molecules and natural products[28,29]. Not surprisingly, the use of T8 gave only trace amount of olefinated products (<2%). Achieving site-selectivity with quinoline, a drastically different molecular scaffold, will require optimization of the templates for precise recognition based on distance and geometry. Considering the broad scope of the covalent nitrile templates for remote C—H activation and ease of synthesis[13-16] we prepared various nitrile-based templates capable of anchoring the first metal through tridendate coordination. While the use of catalytic amount of free templates was not effective, preassembled complexes T11-18 directed remote C—H activation of quinoline with various degrees of efficiency (FIG. 4). Thus, in the presence of catalytic amount of Pd(OAc)$_2$ and mono-protected amino acid ligand (Ac-Gly-OH), olefination of 4a with the optimized complex T18 gave the olefination product 5a in 75% yield with excellent site-selectivity (C5:others=92:8). Notably, the complex T18 was recovered in 96% yield by a simple work-up with 4-dimethylaminopyridine (DMAP) followed by the treatment with methanesulfonic acid in acetonitrile (see Supplementary Information), thus rendering T18 as a recyclable reagent for remote C—H activation. A range of quinolines containing both electron-donating (5b-e) and -withdrawing groups (5f-i, 5k) gave the desired olefination product in good yields and selectivity. The 8-chloro retarded the reaction by weakening the coordination of the nitrogen of quinoline ring (5j). This recyclable non-covalent template T18 is also compatible with other heterocycles including quinoxaline, benzoxazole and benzothiazole (5l-o). The potential utility of this template approach is also demonstrated in a late-stage modification of an antileukemic and antitumor alkaloid (+)-camptothecin[30] (5p).

DOCUMENTS CITED

1. Snieckus, V. Directed ortho metalation. Tertiary amide and O-carbamate directors in synthetic strategies for polysubstituted aromatics. *Chem. Rev.* 90, 879-933 (1990).
2. Flemming, J. P., Berry, M. B. & Brown, J. M. Sequential ortho-lithiations; the sulfoxide group as a relay to enable meta-substitution. *Org. Biomol. Chem.* 6, 1215-1221 (2008).
3. Daugulis, O., Do, H.-Q. & Shabashov, D. Palladium- and copper-catalyzed arylation of carbon-hydrogen bonds. *Acc. Chem. Res.* 42, 1074-1086 (2009).

4. Lyons, T. W. & Sanford, M. S. Palladium-catalyzed ligand-directed C—H functionalization reactions. *Chem. Rev.* 110, 1147-1169 (2010).
5. Colby, D. A., Bergman, R. G. & Ellman, J. A. Rhodium-catalyzed C—C bond formation via heteroatom-directed C—H bond activation. *Chem. Rev.* 110, 624-655 (2010).
6. Breslow, R. Biomimetic control of chemical selectivity. *Acc. Chem. Res.* 13, 170-177 (1980).
7. Das, S. Incarvito, C. D. Crabtree, R. H. & Brudvig, G. W. Molecular recognition in the selective oxygenation of saturated C—H bonds by a dimanganese catalyst. *Science* 312, 1941-1943 (2006).
8. Martinez-Martinez, A. J., Kennedy, A. R., Mulvey, R. E., O'Hara, C. T. Directed ortho-meta'- and meta-meta'-dimetalations: A template base approach to deprotonation. *Science* 346, 834-837 (2014).
9. Phipps, R. J. & Gaunt, M. J. A meta-selective copper-catalyzed C—H bond arylation. *Science* 323, 1593-1597 (2009).
10. Saidi, O. et al. Ruthenium-catalyzed meta sulfonation of 2-phenylpyridines. *J. Am. Chem. Soc.* 133, 19298-19301 (2011).
11. Hofmann, N. & Ackermann, L. Meta-selective C—H bond alkylation with secondary alkyl halides. *J. Am. Chem. Soc.* 135, 5877-5884 (2013).
12. Li, J., et al. N-acyl amino acid ligands for ruthenium (II)-catalyzed meta-C—H tert-alkylation with removable auxiliaries. *J. Am. Chem. Soc.* 137, 13894-13901 (2015).
13. Leow, D., Li, G., Mei, T.-S. & Yu, J.-Q. Activation of remote meta-C—H bonds assisted by an end-on template. *Nature* 486, 518-522 (2012).
14. Lee, S., Lee, H. & Tan, K. L. Meta-selective C—H functionalization using a nitrile-based directing group and cleavable Si-tether. *J. Am. Chem. Soc.* 135, 18778-18781 (2013).
15. Tang, R.-Y., Li, G. & Yu, J.-Q. Conformation-induced remote meta-C—H activation of amines. *Nature* 507, 215-220 (2014).
16. Bera, M., Maji, A., Sahoo, S. K. & Maiti, D. Palladium (II)-catalyzed meta-C—H olefination: constructing multisubstituted arenes through homo-diolefination and sequential hetero-diolefination. *Angew. Chem. Int. Ed.* 54, 8515-8519 (2015).
17. Chu, L. et al. Remote meta-C—H activation using a pyridine-based template: achieving site-selectivity via the recognition of distance and geometry. *ACS Cent. Sci.* 1, 394-399 (2015).
18. Kuninobu, Y., Ida, H., Nishi, M.& Kanai M. A meta-selective C—H borylation directed by a secondary interaction between ligand and substrate. *Nat. Chem.* 7, 712-717 (2015).
19. Shibasaki, M. & Yoshikawa, N. Lanthanide complexes in multifunctional asymmetric catalysis. *Chem. Rev.* 102, 2187-2210 (2002).
20. van den Beuken, E. K. & Feringa, B. L. Bimetallic catalysis by late transition metal complexes. *Tetrahedron* 54, 12985-13011(1998).
21. Konsler, R. G., Karl, J. & Jacobsen, E. N. Cooperative asymmetric catalysis with dimeric Salen complexes. *J. Am. Chem. Soc.* 120, 10780-10781 (1998).
22. Park, J. & Hong, S. Cooperative bimetallic catalysis in asymmetric transformations. *Chem. Soc. Rev.* 41, 6931-6943 (2012).
23. Alvarado, R. J. et al. Structural insights into the coordination and extraction of Pb(II) by disulfonamide ligands derived from o-phenylenediamine. *Inorg. Chem.* 44, 7951-7959 (2005).
24. Cheng P.-H., Cheng H.-Y., Lin C.-C. & Peng S.-M. Oxidations of N,N'-disubstituted o-phenylenediamine in the presence of metal ions and the crystal structure of N,N'-dimethylbenzimidazolium perchlorate, pyridine-bis (o-benzosemiquinonediimine)cobalt(III) chloride and bis (pyridine)(N,N'-bistoluene-p-sulfonyl-o-phenylenediiminato)-copper(II). *Inorg. Chim. Acta.* 169, 19-21(1990).
25. Nakao, Y., Kanyiva, K. S. & Hiyama, T. A strategy for C—H activation of pyridines: direct C-2 selective alkenylation of pyridines by nickel/Lewis acid catalysis. *J. Am. Chem. Soc.* 130, 2448-2449 (2008).
26. Tsai, C.-C. et al. Bimetallic nickel aluminum mediated para-selective alkenylation of pyridine: direct observation of $\eta^2,\eta^1$-pyridine Ni(0)-Al(III) intermediates prior to C—H bond activation. *J. Am. Chem. Soc.* 132, 11887-11889 (2010).
27. Yang, Y.-F. et al. Palladium-catalyzed meta-selective C—H bond activation with a nitrile-containing template: computational study on mechanism and origins of selectivity. *J. Am. Chem. Soc.* 136, 344-355 (2014).
28. Vitaku, E. Smith, D. T. & Njardarson, J. T. Analysis of the structural diversity, substitution patterns, and frequency of nitrogen heterocycles among U.S. FDA approved pharmaceuticals. *J. Med. Chem.* 57, 10257-10274 (2014).
29. Taylor, R. D., MacCoss, M. & Lawson, A. D. G. Rings in drugs. *J. Med. Chem.* 57, 5845-5859 (2014).
30. Stork, G. & Schultz, A. G. The total synthesis of dl-camptothecin. *J. Am. Chem. Soc.* 93, 4074-4075 (1971).

EXAMPLES

1. General Information

Unless otherwise stated, all reagents were purchased from commercial suppliers and used without further purification. Anhydrous solvents were obtained from the solvent purification system produced by JC Meyer Solvent Systems. Analytical thin layer chromatography (TLC) was performed on Merck Millipore precoated (0.25 mm thickness) silica gel plates with F254 indicator. Visualization was accomplished by irradiation with UV light at 254 nm or PMA or $KMnO_4$ stain solution. Flash column chromatography was performed on silica gel (32-63 μm) supplied by Dynamic Adsorbents. $^1H$ NMR spectra were recorded on a Bruker DRX-600 spectrometer (600 MHz) in deuterated solvent and chemical shifts were reported in ppm (δ) relative to tetramethylsilane with the solvent resonance employed as the internal standard ($CDCl_3$, δ 7.26 ppm; DMSO-$d_6$, δ 2.50 ppm; acetonitrile-$d_3$, δ 1.94 ppm). Data are reported as follows: chemical shift, multiplicity (s=singlet, d=doublet, t=triplet, q=quartet, m=multiplet, br=broad), coupling constants (Hz) and integration. $^{13}C$ NMR spectra were recorded on a Bruker DRX-600 spectrometer (151 MHz) in deuterated solvent with complete proton decoupling and chemical shifts are reported in ppm from tetramethylsilane with the solvent resonance as the internal standard ($CDCl_3$, δ 77.0 ppm; DMSO-$d_6$, δ 39.5 ppm; acetonitrile-$d_3$, δ 1.32 ppm). High-resolution mass spectra (HRMS) were recorded on an Agilent LC/MSD TOF mass spectrometer. The single crystal X-ray diffraction studies were carried out on a Bruker Kappa APEX-II CCD diffractometer equipped with Mo K radiation (λ=0.71073 Å). The substrates 1b-v were synthesized according to the literature known procedures[1,2].

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like. HFIP refers to 1,1,1,3,3,3-hexafluoro-2-propanol.

2. General Procedure for Synthesis of Bisdentate Templates T1-10

2.1 Procedure for Synthesis of T1, T3-7, T9-10

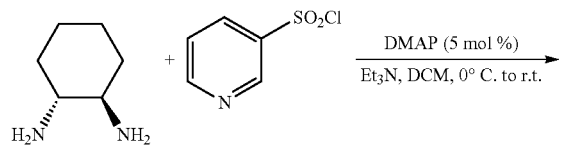

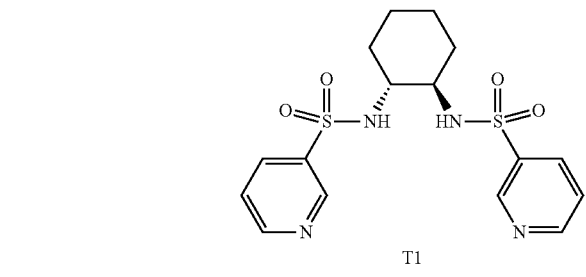

(1R,2R)-cyclohexane-1,2-diamine (343 mg, 3.0 mmol) and DMAP (18 mg, 0.15 mmol) were placed in a pre-dried 100 mL three-necked flask and flushed with nitrogen. DCM (25 mL) and $Et_3N$ (1.25 mL, 9.0 mmol) were added into the flask under nitrogen. The reaction solution was cooled to 0° C. and pyridine-3-sulfonyl chloride (0.75 mL, 6.3 mmol) was added dropwise. The reaction mixture was stirred at 0° C. for 2 hours and warmed to room temperature slowly then stirred overnight. The solvent and volatile compounds were evaporated under reduced pressure at 45° C. The residue was purified by column chromatography on silica gel using DCM/MeOH (20:1) as the eluent giving the template T1 in its pure form.

2.2 Procedure for Synthesis of T8

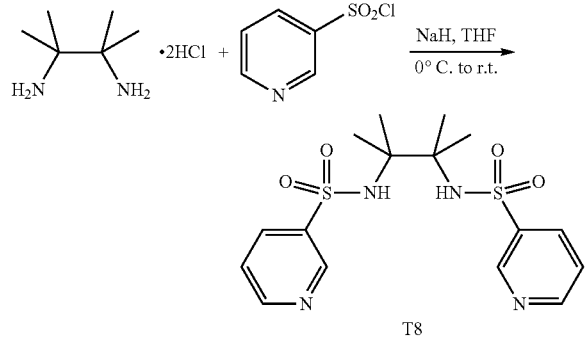

Sodium hydride (1.476 g, 36.9 mmol, 60% dispersion in mineral oil) was placed in a pre-dried 50 mL Schlenk flask under nitrogen. THF (10 mL) was added and the mixture was cooled to 0° C. 2,3-Dimethyl-2,3-butanediamine dihydrochloride (698 mg, 3.69 mmol) was added into the flask in portions under nitrogen, the mixture was stirred at 0° C. for 0.5 hour then warmed to room temperature and stirred for 0.5 hour. The mixture was cooled to 0° C. and pyridine-3-sulfonyl chloride (1.32 mL, 11.07 mmol) was added dropwise. The reaction mixture was stirred at 0° C. for 2 hours and warmed to room temperature slowly then stirred overnight. 2 N aqueous solution of HCl (11 mL) was added at 0° C. slowly and the mixture was extracted with ethyl acetate (50 mL) and DCM (50 mL) three times respectively. The organic layers were then combined and dried with $Na_2SO_4$. After removal of the solvents, the residue was purified by column chromatography on silica gel using DCM/MeOH (20:1) as the eluent giving the template T8 in its pure form. Templates T2[3], T4[4], T5[5], T9[6] and T10[7] have been synthesized and characterized before.

3. General Procedure for Remote Site-Selective C—H Olefination of Substrates 1

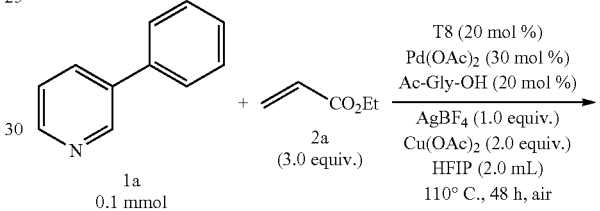

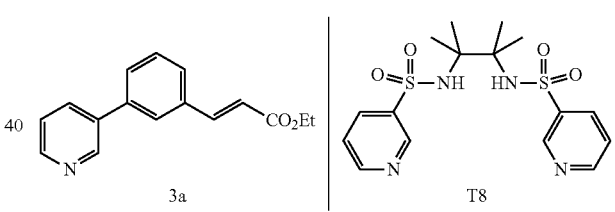

A reaction tube (15 mL) with magnetic stir bar was charged with 1a (14.3 µL, 0.1 mmol), T8 (8.0 mg, 0.02 mmol), Pd(OAc)$_2$ (6.7 mg, 0.03 mmol), Ac-Gly-OH (2.3 mg, 0.02 mmol), AgBF$_4$ (19.5 mg, 0.1 mmol), Cu(OAc)$_2$ (36.3 mg, 0.2 mmol), HFIP (2.0 ml) and 2a (31.8 µl, 0.3 mmol) in air. The reaction tube was sealed and allowed to stir at ambient temperature for 10 minutes, then heated to 110° C. for 48 hours. Upon completion, the reaction mixture was cooled to 0° C. and saturated aqueous solution of sodium sulfide (1.0 mL) was added followed by water (3.0 mL). The mixture was extracted with DCM (10 mL) for three times and the organic layers were combined and filtered through a silica gel plug then dried with $Na_2SO_4$. The solvent and volatile compounds were evaporated under reduced pressure at 45° C. The crude reaction mixture was purified on preparative TLC using hexanes/ethyl acetate (2:1) as the eluent to afford the desired product 3a.

Caution: The operator should have appropriate protection all the time when the reaction is running due to the high pressure generated in the sealed reaction flask under high temperature.

4. Optimization of Reaction Conditions 4.1 Screening of the Palladium Salts

TABLE S1

Screening of the Palladium Salts

| Entry | Pd(II) | Yield (%)[a] | m:(o + p)[a] |
|---|---|---|---|
| 1 | Pd(CH$_3$CN)$_2$(BF$_4$)$_2$ | 2 | 79:21 |
| 2 | Pd(TFA)$_2$ | 7 | 73:27 |
| 3 | Pd(acac)$_2$ | 1 | 60:40 |
| 4 | PdSO$_4$ | 1 | 70:30 |
| 5 | PdCl$_2$ | <1 | N.D. |
| 6 | Pd(OAc)$_2$ | 49 | 73:27 |

[a]The yield of the olefinated products, the meta:(ortho + para) ratio of mono-olefinated products were determined by $^1$H NMR analysis of the unpurified reaction mixture using CH$_2$Br$_2$ as the internal standard (assistd with GC-MS analysis), the variance isestimated to be within 5%. Ac-Gly-OH: N-acetyl-glycine.

4.2 Screening of the Silver Salts

TABLE S2

Screening of the Silver Salts

| Entry | Ag(I) | Yield (%)[a] | m:(o + p)[a] |
|---|---|---|---|
| 1 | AgTFA | 21 | 63:37 |
| 2 | AgOTf | 29 | 63:37 |
| 3 | AgF | 4 | 63:37 |
| 4 | AgPF$_6$ | 14 | 71:29 |
| 5 | AgSbF$_6$ | 23 | 66:34 |
| 6 | AgBF$_4$ | 32 | 72:28 |

[a]The yield of the olefinated products, the meta:(ortho + para) ratio of mono-olefinated products were determined by $^1$H NMR analysis of the unpurified reaction mixture using CH$_2$Br$_2$ as the internal standard (assisted with GC-MS analysis), the variance is estimated to be within 5%. Ac-Gly-OH: N-acetyl-glycine.

4.3 Screening of the Oxidants/Additives

TABLE S3

Screening of the Oxidants/Additives

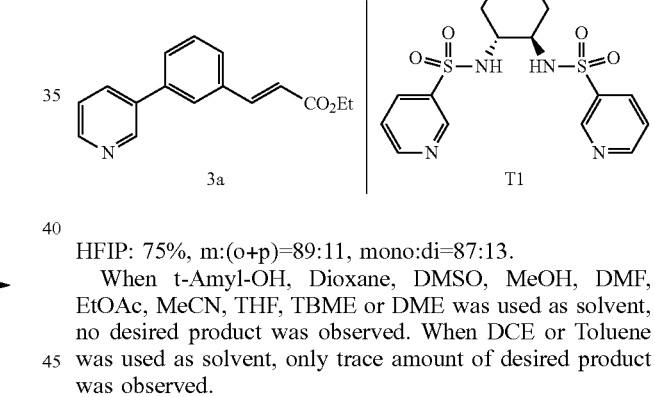

| Entry | Additive (2.0 equiv. of Cu) | Yield (%)[a] | m:(o + p)[a] |
|---|---|---|---|
| 1 | Cu(OTf)$_2$ | 0 | N.D. |
| 2 | Cu(TFA)$_2$ · xH$_2$O | 0 | N.D. |
| 3 | Cu$_3$(PO$_4$)$_2$ | 33 | 84:16 |
| 4 | CuCl$_2$ | 0 | N.D. |
| 5 | CuF$_2$ | 45 | 85:15 |
| 6 | CuO | 34 | 81:19 |
| 7 | Cu(NO$_3$)$_2$ · 3H$_2$O | 0 | N.D. |
| 8 | Cu(ClO$_4$)$_2$ · 6H$_2$O | 0 | N.D. |
| 9 | Cu(TCA)$_2$ | 0 | N.D. |
| 10 | Cu(OAc)$_2$ | 53 | 85:15 |

[a]The yield of the olefinated products, the meta:(ortho + para) ratio of mono-olefinated products were determined by $^1$H NMR analysis of the unpurified reaction mixture using CH$_2$Br$_2$ as the internal standard (assisted with GC-MS analysis), the variance is estimated to be within 5%.

4.4 Screening of the Solvents

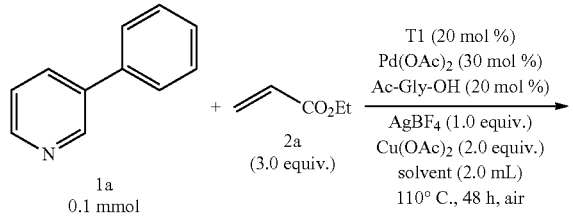

HFIP: 75%, m:(o+p)=89:11, mono:di=87:13.

When t-Amyl-OH, Dioxane, DMSO, MeOH, DMF, EtOAc, MeCN, THF, TBME or DME was used as solvent, no desired product was observed. When DCE or Toluene was used as solvent, only trace amount of desired product was observed.

4.5 Screening of the Loading of 2a

TABLE S4

Screening of the loading of 2a

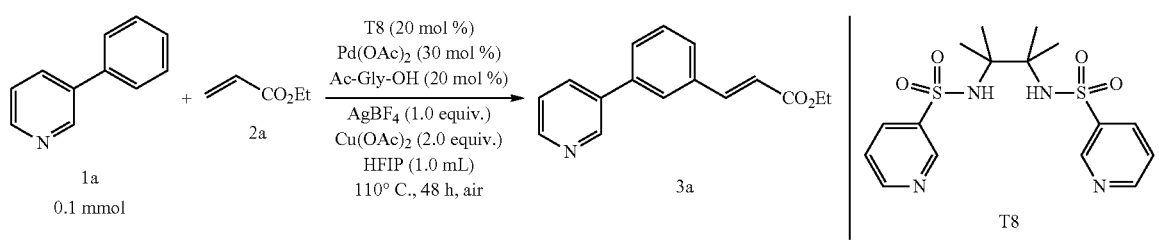

TABLE S4-continued

| Entry | 2a (equiv.) | Yield (%)[a] | m:(o + p)[a] |
|---|---|---|---|
| 1 | 5.0 | 60 | 94.4:5.6 |
| 2 | 4.0 | 66 | 94.0:6.0 |
| 3 | 3.0 | 75 | 94.3:5.7 |
| 4 | 2.0 | 70 | 93.8:6.2 |

[a]The yield of the olefinated products, the meta:(ortho + para) ratio of mono-olefinated products were determined by $^1$H NMR analysis of the unpurified reaction mixture using $CH_2Br_2$ as the internal standard (assisted with GC-MS analysis), the variance is estimated to be within 5%.

4.6 Screening of the Concentrations

TABLE S5

Screening of the Concentrations

| Entry | HFIP (mL) | Concentration (M) | Yield (%)[a] | m:(o + p)[a] |
|---|---|---|---|---|
| 1 | 1.0 | 0.100 | 75 | 94:6 |
| 2 | 2.0 | 0.050 | 77 | 95:5 |
| 3 | 3.0 | 0.033 | 69 | 95:5 |
| 4 | 4.0 | 0.025 | 57 | 94:6 |
| 5 | 5.0 | 0.020 | 51 | 93:7 |

[a]The yield of the olefinated products, the meta:(ortho + para) ratio of mono-olefinated products were determined by $^1$H NMR analysis of the unpurified reaction mixture using $CH_2Br_2$ as the internal standard (assisted with GC-MS analysis), the variance is estimated to be within 5%.

4.7 Screening of the Loading of Template, Pd(OAc)$_2$ and Ligand

TABLE S6

Screening of the Loading of Template, Pd(OAc)$_2$ and Ligand

| Entry | T8 (mol %) | Pd(OAc)$_2$ (mol %) | Ac-Gly-OH (mol %) | Yield (%)[a] | m:(o + p)[a] |
|---|---|---|---|---|---|
| 1 | 10 | 15 | 10 | 14 | 89:11 |
| 2 | 10 | 15 | 15 | 25 | 90:10 |
| 3 | 10 | 20 | 5 | 62 | 94:6 |
| 4 | 10 | 20 | 10 | 60 | 94:6 |
| 5 | 10 | 20 | 15 | 40 | 92:8 |
| 6 | 15 | 20 | 5 | 64 | 95:5 |
| 7 | 15 | 30 | 15 | 65 | 95:5 |
| 8 | 20 | 30 | 10 | 76 | 95:5 |
| 9 | 20 | 30 | 20 | 77 | 95:5 |

[a]The yield of the olefinated products, the meta:(ortho + para) ratio of mono-olefinated products were determined by $^1$H NMR analysis of the unpurified reaction mixture using $CH_2Br_2$ as the internal standard (assisted with GC-MS analysis), the variance is estimated to be within 5%.

5. Gram-Scale Reaction

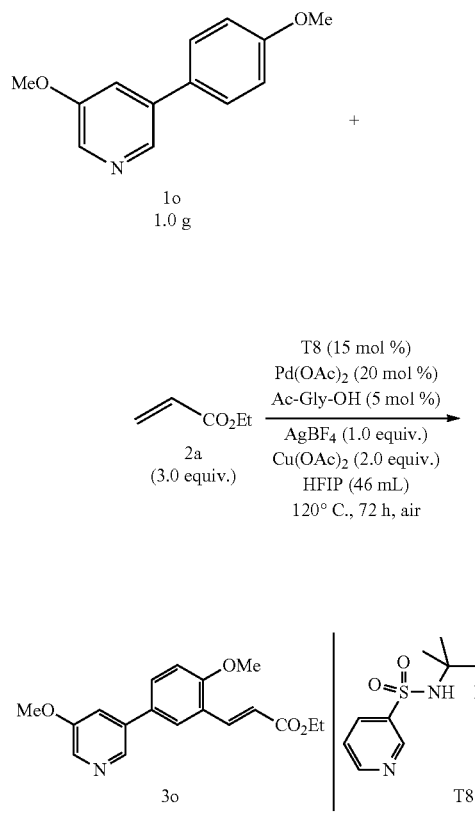

A reaction tube (250 mL) with magnetic stir bar was charged with 1o (1.0 g, 4.646 mmol), T8 (277 mg, 0.697 mmol), Pd(OAc)$_2$ (209 mg, 0.929 mmol), Ac-Gly-OH (27 mg, 0.232 mmol), AgBF$_4$ (0.904 g, 4.646 mmol), Cu(OAc)$_2$ (1.688 g, 9.292 mmol), HFIP (46 ml) and 2a (1.48 mL, 13.937 mmol) in air. The reaction tube was sealed and allowed to stir at ambient temperature for 10 minutes, then heated to 120° C. for 72 hours. Upon completion, the reaction mixture was cooled to 0° C. and saturated aqueous solution of sodium sulfide (10 mL) was added followed by water (30 mL) and DCM (30 mL). The mixture was filtered through a pad of celite and washed with DCM. The solvents were evaporated under reduced pressure at 45° C. and then the mixture was extracted with DCM (100 mL) for three times. After dried with Na$_2$SO$_4$, the solvent and volatile compounds were evaporated under reduced pressure at 45° C. A sample (10 mg) was taken from the unpurified reaction mixture and the m:o ratio of mono-olefinated products was determined to be 99:1 and the mono:di ratio was determined to be 98:2 by $^1$H NMR analysis. The rest crude reaction mixture and the sample for $^1$H NMR analysis were combined and purified by column chromatography on silica gel using hexane/ethyl acetate (5:1 to 2:1) then DCM/MeOH (10:1) as the eluents giving 3o (1.03 g, 70% yield) and T8 (266 mg, 96% recovered).

Caution: The operator should have appropriate protection all the time when the reaction is running due to the high pressure generated in the sealed reaction flask under high temperature.

6. General Procedure for Synthesis of Tridentate Templates T11-19

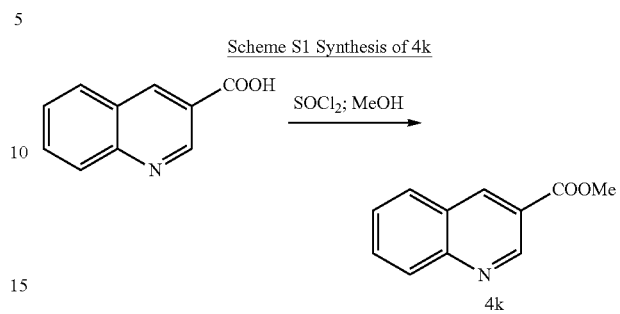

Scheme S1 Synthesis of 4k

Quinoline-3-carboxylic acid (0.245 g, 1.41 mmol) was charged in the flask with stir bar and thionyl chloride was added. The resulting mixture was allowed to stir at 80° C. overnight. Upon completion, the reaction mixture was cooled to room temperature and concentrated in vacuo. MeOH was added to this crude mixture and was heated under reflux for 8 h. Upon completion, the reaction mixture was cooled to room temperature, diluted with DCM, and was washed with saturated aqueous NaHCO$_3$. The aqueous layer was extracted with DCM twice, and the combined organic layers were dried with anhydrous Na$_2$SO$_4$. After removal of the solvents, the residue was purified by column chromatography on silica gel using EtOAc/hexanes (1:6) as the eluent to give 4k (0.161 g, 61%). $^1$H NMR (600 MHz, CDCl$_3$): δ 9.46 (d, J=2.1 Hz, 1H), 8.86 (d, J=2.2 Hz, 1H), 8.17 (d, J=8.5 Hz, 1H), 7.95 (d, J=8.2 Hz, 1H), 7.84 (ddd, J=8.5, 6.9, 1.4 Hz, 1H), 7.63 (ddd, J=8.1, 6.9, 1.2 Hz, 1H), 4.03 (s, 3H). $^1$H NMR matches previously reported data[8].

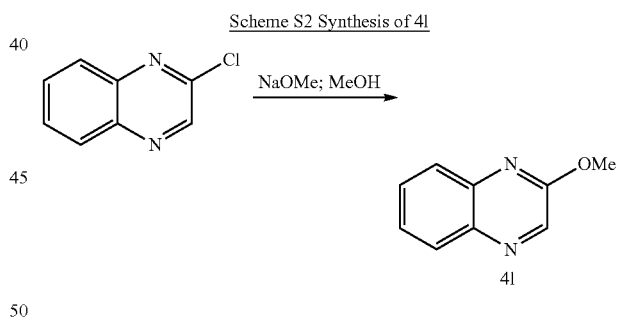

Scheme S2 Synthesis of 4l

2-Chloroquinoxaline (0.823 g, 5 mmol) and NaOMe (1.89 g, 35 mmol) were charged in the flask with stir bar and MeOH (10 mL) was added to this mixture. The resulting solution was heated at 80° C. for 4 h. Upon completion, the reaction mixture was cooled to room temperature and filtered through celite (the celite pad was washed with EtOAc). The filtrate was concentrated in vacuo. Water was added to this crude mixture and extracted with EtOAc three times. The combined organic layers were dried with anhydrous Na$_2$SO$_4$. After removal of the solvents, the residue was purified by column chromatography on silica gel using EtOAc/hexanes as the eluent giving pure product. $^1$H NMR (600 MHz, CDCl$_3$): δ 8.47 (s, 1H), 8.02 (dd, J=8.2, 1.5 Hz, 1H), 7.85 (dd, J=8.3, 1.4 Hz, 1H), 7.67 (ddd, J=8.4, 7.0, 1.5 Hz, 1H), 7.56 (ddd, J=8.3, 7.0, 1.4 Hz, 1H), 4.10 (s, 3H); $^{13}$C NMR (151 MHz, CDCl$_3$): δ 157.67, 140.38, 139.59, 138.87, 130.09, 128.98, 127.18, 126.51, 53.69. $^1$H NMR, $^{13}$C NMR matches previously reported data[9].

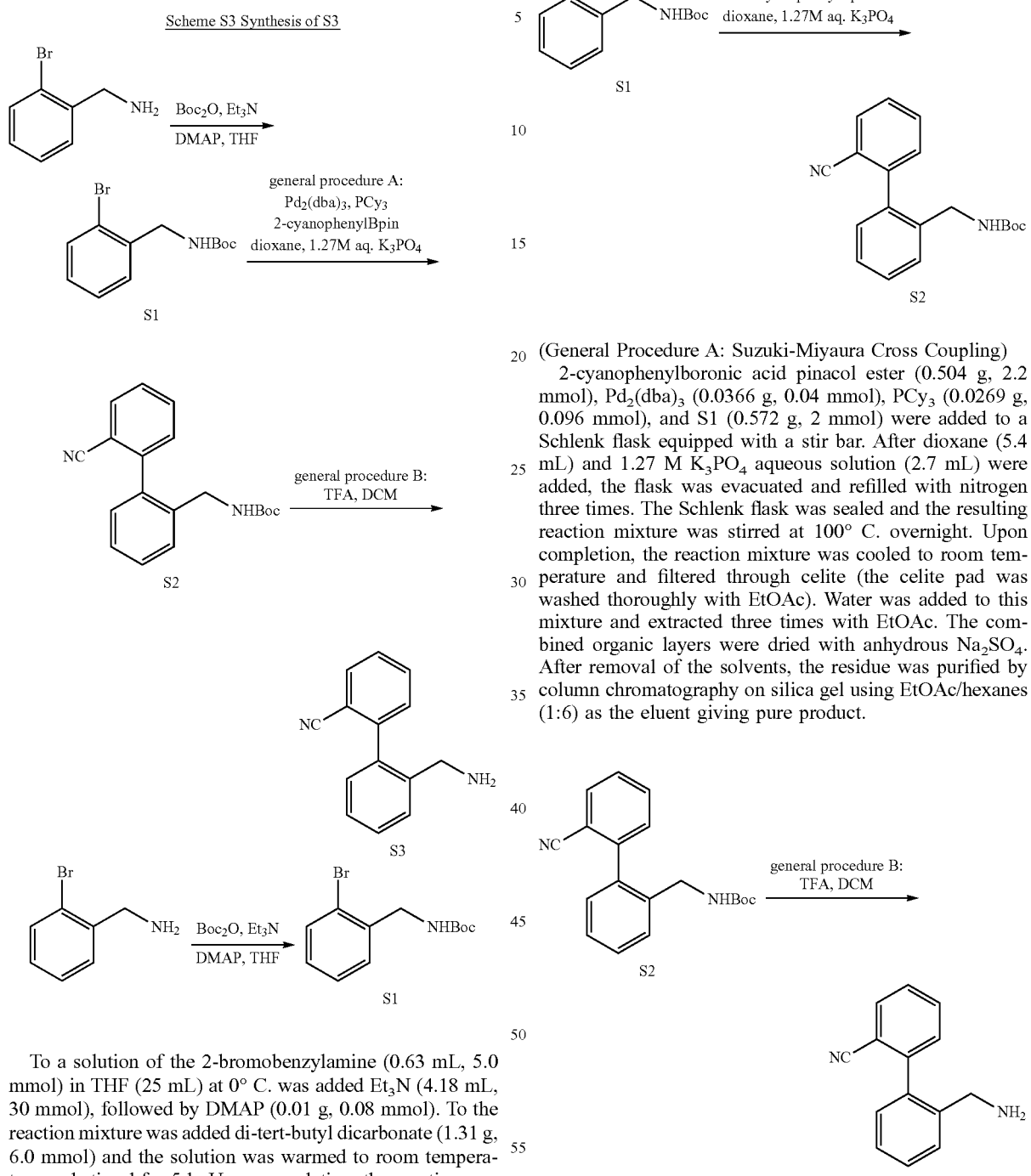

Scheme S3 Synthesis of S3

To a solution of the 2-bromobenzylamine (0.63 mL, 5.0 mmol) in THF (25 mL) at 0° C. was added Et$_3$N (4.18 mL, 30 mmol), followed by DMAP (0.01 g, 0.08 mmol). To the reaction mixture was added di-tert-butyl dicarbonate (1.31 g, 6.0 mmol) and the solution was warmed to room temperature and stirred for 5 h. Upon completion, the reaction was quenched with cold water and extracted with EtOAc three times. The combined organic layers were washed with water and brine, dried with anhydrous Na$_2$SO$_4$, and concentrated. The residue was purified by column chromatography on silica gel using EtOAc/hexanes (1:10) as the eluent giving the pure product. $^1$H NMR (400 MHz, CDCl$_3$): δ 7.54 (dd, J=8.0, 1.3 Hz, 1H), 7.38 (d, J=7.7 Hz, 1H), 7.29 (d, J=7.4, 1.2 Hz, 1H), 7.14 (dd, J=7.8, 1.8 Hz, 1H), 5.01 (br, 1H), 4.39 (d, J=6.3 Hz, 2H), 1.45 (s, 9H). $^1$H NMR matches previously reported data[10].

(General Procedure A: Suzuki-Miyaura Cross Coupling)

2-cyanophenylboronic acid pinacol ester (0.504 g, 2.2 mmol), Pd$_2$(dba)$_3$ (0.0366 g, 0.04 mmol), PCy$_3$ (0.0269 g, 0.096 mmol), and S1 (0.572 g, 2 mmol) were added to a Schlenk flask equipped with a stir bar. After dioxane (5.4 mL) and 1.27 M K$_3$PO$_4$ aqueous solution (2.7 mL) were added, the flask was evacuated and refilled with nitrogen three times. The Schlenk flask was sealed and the resulting reaction mixture was stirred at 100° C. overnight. Upon completion, the reaction mixture was cooled to room temperature and filtered through celite (the celite pad was washed thoroughly with EtOAc). Water was added to this mixture and extracted three times with EtOAc. The combined organic layers were dried with anhydrous Na$_2$SO$_4$. After removal of the solvents, the residue was purified by column chromatography on silica gel using EtOAc/hexanes (1:6) as the eluent giving pure product.

(General Procedure B: Deprotection of Boc Protecting Group)

To a solution of the S2 (0.64 g, 2 mmol) in DCM (32 mL) at 0° C. was added TFA (3 mL) slowly. The solution was warmed to room temperature and stirred for 2 hours. Upon completion, the reaction was quenched with saturated aqueous NaHCO$_3$ and the organic layer was separated. Water layer was extracted with DCM three times and the combined organic layers were dried with anhydrous Na$_2$SO$_4$, and concentrated to give the crude amine S3, which was used in the next step without further purification.

Scheme S4 Synthesis of S4

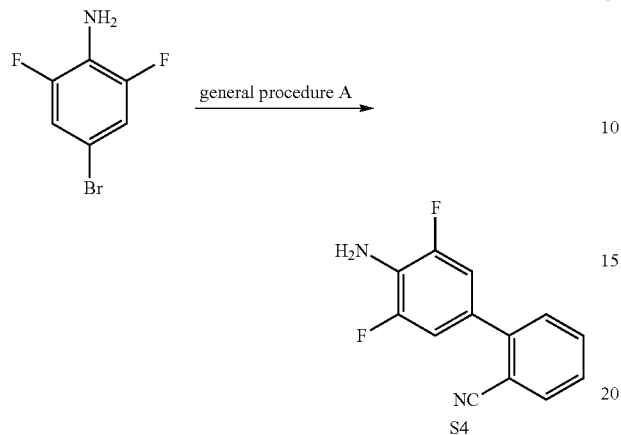

S4 was synthesized using general procedure A and was purified by column chromatography on silica gel using EtOAc/hexanes (1:10) as the eluent.

Scheme S5 Synthesis of S5 and S6

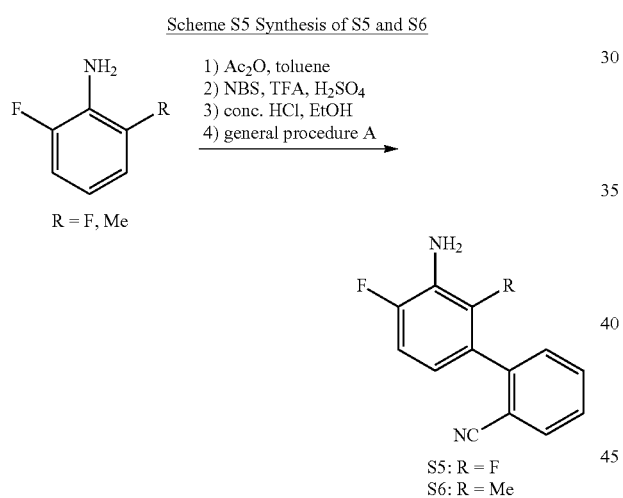

For S5 (R = F)

To a solution of 2,6-difluoroaniline (1.0 mL, 10 mmol) in toluene (20 mL) was added acetic anhydride (1.13 mL, 12 mmol) in one portion. The reaction mixture was allowed to stir overnight at 110° C. Upon completion, the solvent was removed under reduced pressure. Water was added to this crude mixture and extracted with EtOAc three times. The combined organic layers were washed with brine and dried with anhydrous $Na_2SO_4$. The solvent was removed to afford N-(2,6-difluorophenyl)acetamide, which was used in the next step without further purification.

To a solution of N-(2,6-difluorophenyl)acetamide in TFA (8.2 mL) and $H_2SO_4$ (11 mL) at 0° C. was added NBS (1.72 g, 9.7 mmol) in portions. The reaction mixture was stirred at 0° C. for 10 min and warmed to room temperature slowly then stirred overnight. Upon completion, ice was added to the reaction mixture and the white precipitate was collected by filtration. The crude product was washed with water and hexane extensively to give N-(3-bromo-2,6-difluorophenyl)acetamide, which was used in the next step without further purification.

To a solution of N-(3-bromo-2,6-difluorophenyl)acetamide in EtOH (5.7 mL) was added concentrated HCl (5.7 mL) at room temperature. The reaction mixture was allowed to stir overnight at 75° C. Upon completion, the reaction mixture was cooled to room temperature. The reaction mixture was cooled to 0° C. and basified with aqueous NaOH solution. The reaction mixture was extracted three times with EtOAc. The combined organic layers were dried with anhydrous $Na_2SO_4$ and concentrated in vacuo to give 3-bromo-2,6-difluoroaniline, which was used in the next step without further purification.

3-bromo-2,6-difluoroaniline was converted to S5 using general procedure A and was purified by column chromatography on silica gel using EtOAc/hexanes as the eluent.

S6 was synthesized using the analogous procedure as S5.

Scheme S6 Synthesis of S10 and S11

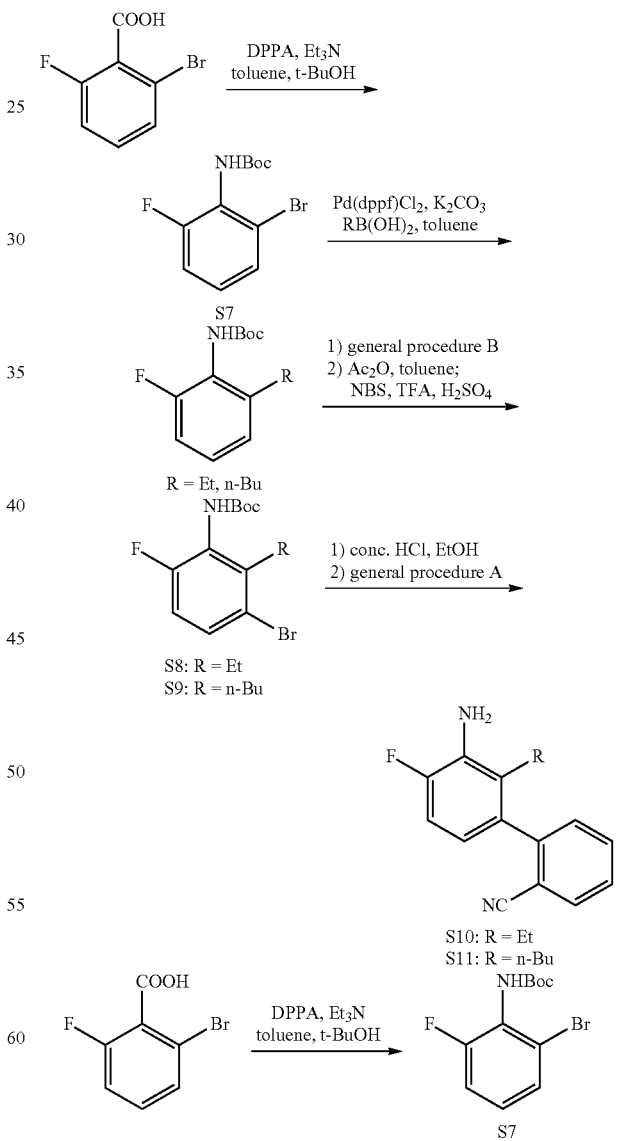

To a solution of the 2-bromo-6-fluorobenzoic acid (2.19 g, 10 mmol) in toluene (40 mL) at room temperature was added Et₃N (1.46 mL, 10.5 mmol), followed by DPPA (2.26 mL, 10.5 mL). The reaction mixture was gradually heated to 70° C. and stirred at the same temperature until bubling stops. The solution was heated to 110° C. After 1 h, to the reaction mixture was added ᵗBuOH (7.4 g) and the solution was allowed to stir overnight at the same temperature. Upon completion, the reaction was cooled down to room temperature. Water was added and extracted with EtOAc three times. The combined organic layers were washed with 0.1 M HCl, water, saturated aqueous NaHCO₃, and brine, dried with anhydrous Na₂SO₄, and concentrated. The residue was purified by column chromatography on silica gel using EtOAc/hexanes (1:20 to 1:10) as the eluent to give S7 (1.69 g, 58%). $^1$H NMR (600 MHz, CDCl₃): δ 7.39-7.35 (m, 1H), 7.10-7.06 (m, 2H), 6.07 (br, 1H), 1.50 (s, 9H). $^1$H NMR matches previously reported data[11].

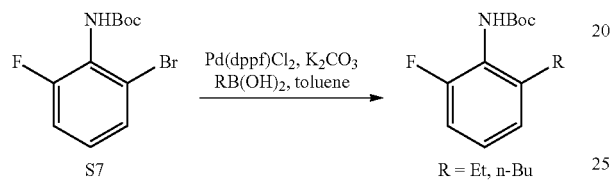

For S8 (R=Et)
In the air, ethylboronic acid (3.69 g, 49.8 mmol), Pd(dppf)Cl₂ (0.91 g, 1.25 mmol), K₂CO₃ (10.3 g, 74.7 mmol), and S7 (7.23 g, 24.9 mmol) were added to a Schlenk flask equipped with a stir bar. After toluene was added, the flask was evacuated and refilled with nitrogen three times. The schlenk flask was sealed and the resulting reaction mixture was stirred at 110° C. overnight. Upon completion, the reaction mixture was cooled to room temperature and filtered through celite (the celite pad was washed thoroughly with EtOAc). The filtrate was concentrated under reduced pressure, and the crude mixture was diluted with DCM, washed with brine, dried over anhydrous Na₂SO₄, filtered, and concentrated under reduced pressure. The mixture was passed through a pad of silica gel using EtOAc/hexanes (1:10) as the eluent to give tert-butyl (2-ethyl-6-fluorophenyl)carbamate, which was used in the next step without further purification.

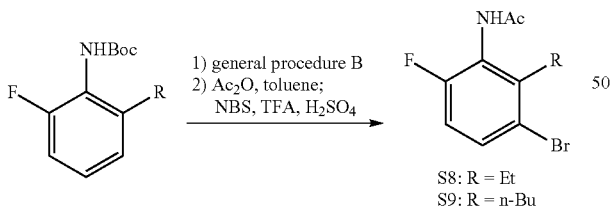

Tert-butyl (2-ethyl-6-fluorophenyl)carbamate was converted to 2-ethyl-6-fluoroaniline using general procedure B. To a solution of 2-ethyl-6-fluoroaniline in toluene was added acetic anhydride (1.3 mL, 13.7 mmol) in one portion. The reaction mixture was allowed to stir overnight at 110° C. Upon completion, the solvent was removed under reduced pressure. To this crude residue was added TFA (12.1 mL) and H₂SO₄ (16.3 mL). The reaction mixture was cooled to 0° C. and NBS (2.44 g, 13.7 mmol) was added in portions. The reaction mixture was stirred at 0° C. for 10 min and warmed to room temperature slowly then stirred overnight.

Upon completion, ice was added to the reaction mixture and the white precipitate was collected by filtration. The crude product was washed with water and hexane extensively, followed by recrystallization from hot MeOH to give S8 (1.55 g, 44%).

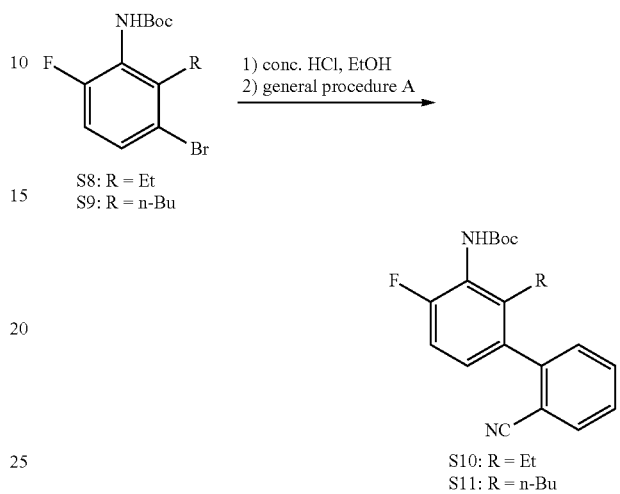

To a solution of S8 (1.43 g, 5.48 mmol) in EtOH (3.7 mL) was added concentrated HCl (3.7 mL) at room temperature. The reaction mixture was allowed to stir overnight at 75° C. Upon completion, the reaction mixture was cooled to room temperature. The reaction mixture was cooled to 0° C. and basified with aqueous NaOH solution. The reaction mixture was extracted three times with EtOAc. The combined organic layers were dried with anhydrous Na₂SO₄ and concentrated in vacuo to give the crude product. This product was used in the next step without further purification.

3-bromo-2-ethyl-6-fluoroaniline was converted to S10 using general procedure A and was purified by column chromatography on silica gel using EtOAc/hexanes (1:10) as the eluent.

S11 was synthesized from S9 in the same manner as S10.

Scheme S7 Synthesis of S14

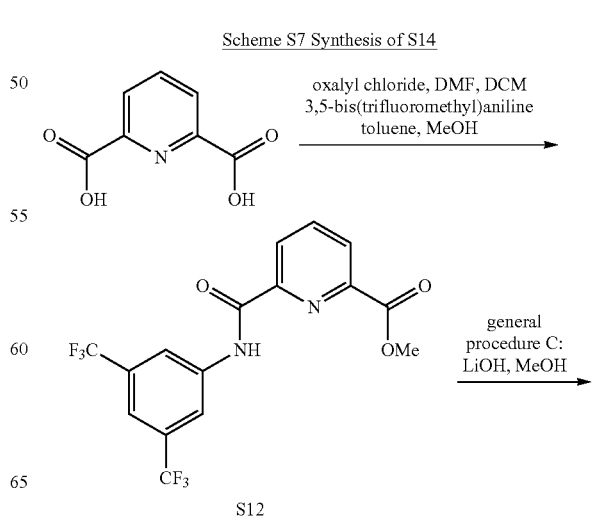

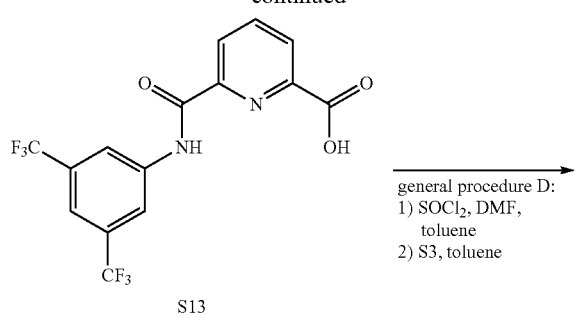

S13

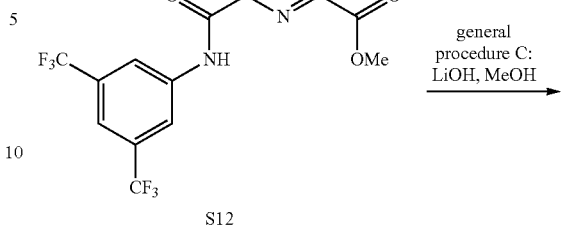

S12

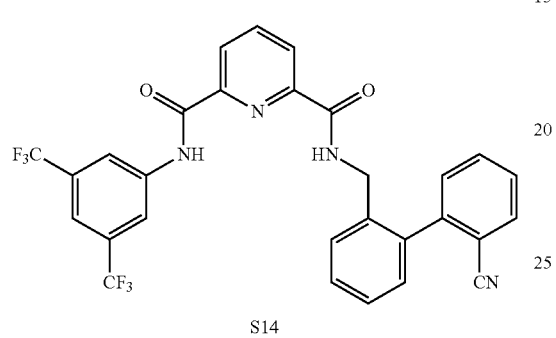

S14

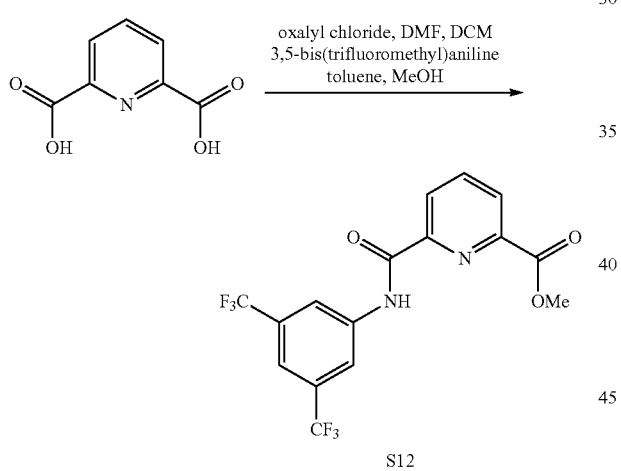

S12

To a solution of 2,6-pyridinedicarboxylic acid (3.34 g, 20 mmol) in DCM (60 mL) was added oxalyl chloride (4 mL, 47.3 mmol) dropwise at room temperature. DMF (3 drops) was added and the reaction mixture was stirred for 10 h. Upon completion, the reaction mixture was concentrated under reduced pressure. Next, toluene (300 mL) and 3,5-bis(trifluoromethyl) aniline (2.5 mL, 16 mmol) were added to the reaction flask and submerged into an oil bath preheated to 70° C. Then, the oil bath was heated to 120° C. and the reaction mixture was allowed to stir overnight. Upon completion, the reaction mixture was cooled to room temperature and concentrated under reduced pressure. MeOH (60 mL) was added to the reaction flask and heated under reflux for 9 h. Upon completion, the reaction mixture was cooled to room temperature. The white precipitate was collected by filtration and recrystallized from hot MeOH to give S12 (1.93 g, 25%).

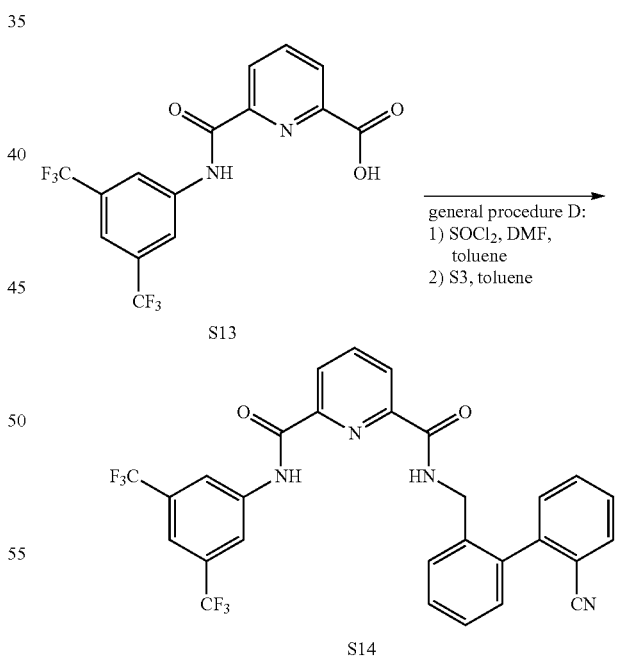

S13

(General Procedure C: Deprotection of Methyl Ester)

To a solution of S12 (1.84 g, 4.69 mmol) in MeOH (55 mL) was added LiOH monohydrate (0.39 g, 9.4 mmol) in portions. Upon completion, the solvent was removed in vacuo. The crude residue was dissolved in water and acidified by 6 M HCl, extracted with EtOAc three times, dried with anhydrous $Na_2SO_4$, and concentrated. The crude product was used in the next step without further purification.

S13

S14

(General Procedure D: Amide Formation)

To a solution of S13 (1.0 equiv.) in toluene was added thionyl chloride (2.5 equiv.) dropwise at room temperature. DMF (3 drops) was added and the reaction mixture was stirred at 80° C. Upon completion, the reaction mixture was concentrated under reduced pressure. Next, toluene and the aniline derivative (e.g. S3 in this example) were added to the reaction flask and submerged into an oil bath pre-heated to 80° C. Then, the oil bath was heated to 120° C. and the reaction mixture was allowed to stir overnight. Upon completion, the reaction mixture was cooled to room temperature and concentrated under reduced pressure. Pure product was isolated by recrystallization from hot MeOH. S15-S19 were synthesized following the same procedure as S14. S18 and S19 were recrystallized from hot MeOH. S16 was purified by column chromatography on silica gel using EtOAc/hexanes as the eluent. S15 and S17 were purified by trituration with DCM, MeOH, and Acetone.

To a solution of 2,6-pyridinecarboxylic acid (1.67 g, 10 mmol) in MeOH (57 mL) was added H$_2$SO$_4$ (0.19 mL) slowly at room temperature. The resulting mixture was allowed to stir at 90° C. overnight. Upon completion, solvent was removed in vacuo. To this residue was added DCM and saturated aqueous NaHCO$_3$. Water layer was extracted with DCM three times. The combined organic layers were dried with anhydrous Na$_2$SO$_4$, and concentrated. Recrystallization from hot MeOH gave S20 (1.49 g, 76%) as colorless crystals. $^1$H NMR (600 MHz, CDCl$_3$): δ 8.33 (d, J=9.7 Hz, 2H), 8.04 (t, J=7.8 Hz, 1H), 4.04 (s, 6H). $^1$H NMR matches previously reported data[12].

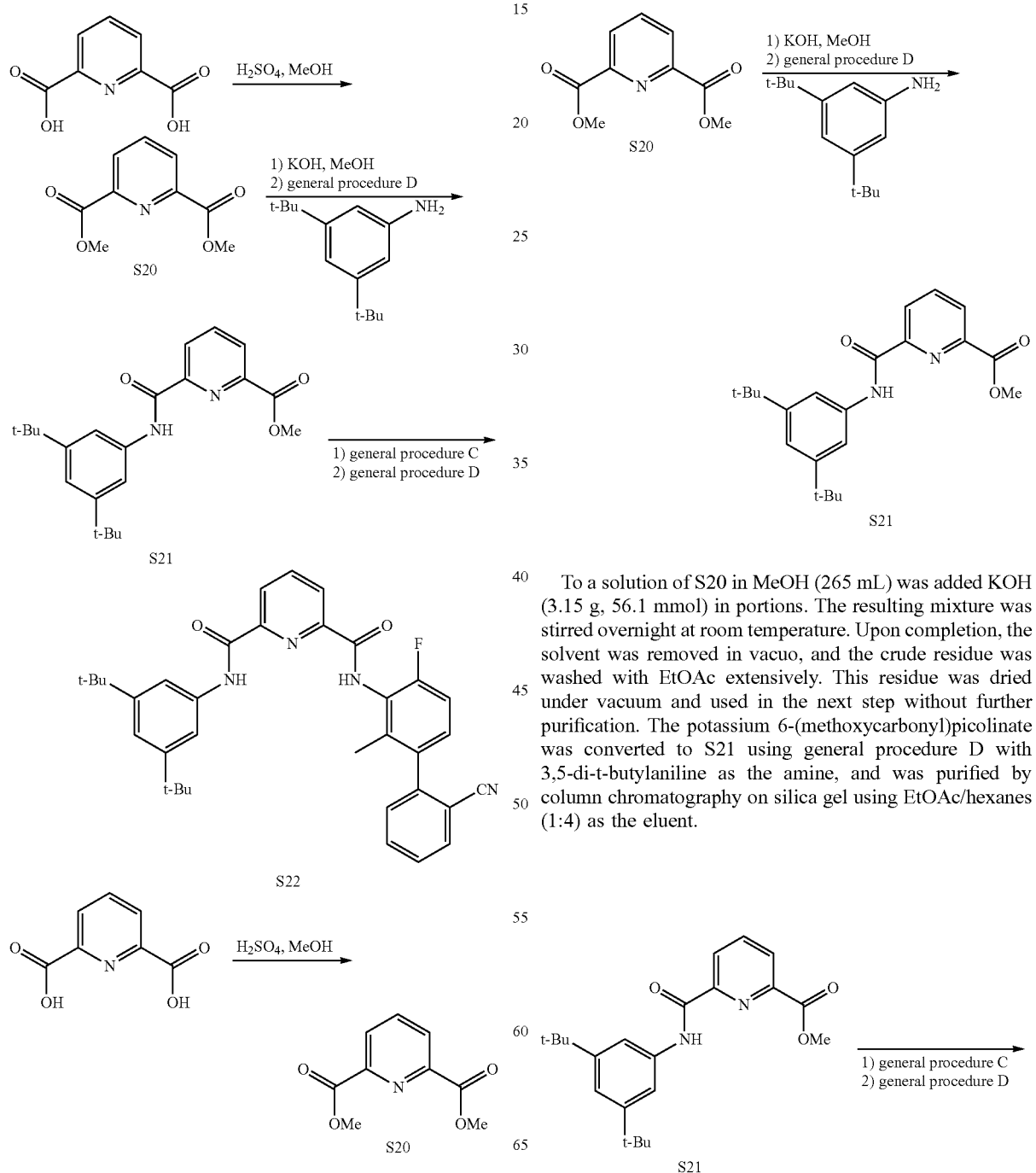

To a solution of S20 in MeOH (265 mL) was added KOH (3.15 g, 56.1 mmol) in portions. The resulting mixture was stirred overnight at room temperature. Upon completion, the solvent was removed in vacuo, and the crude residue was washed with EtOAc extensively. This residue was dried under vacuum and used in the next step without further purification. The potassium 6-(methoxycarbonyl)picolinate was converted to S21 using general procedure D with 3,5-di-t-butylaniline as the amine, and was purified by column chromatography on silica gel using EtOAc/hexanes (1:4) as the eluent.

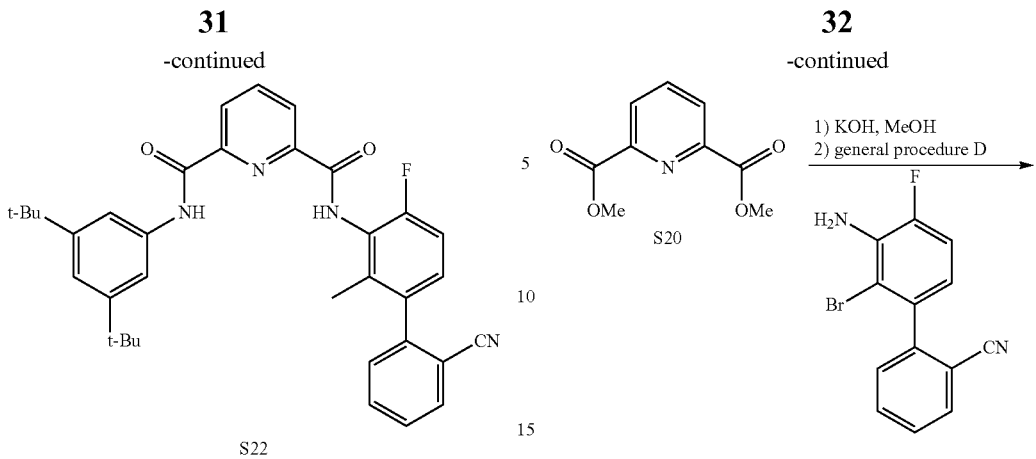

S21 was converted to S22 using general procedure C and D, then recrystallized from hot MeOH.

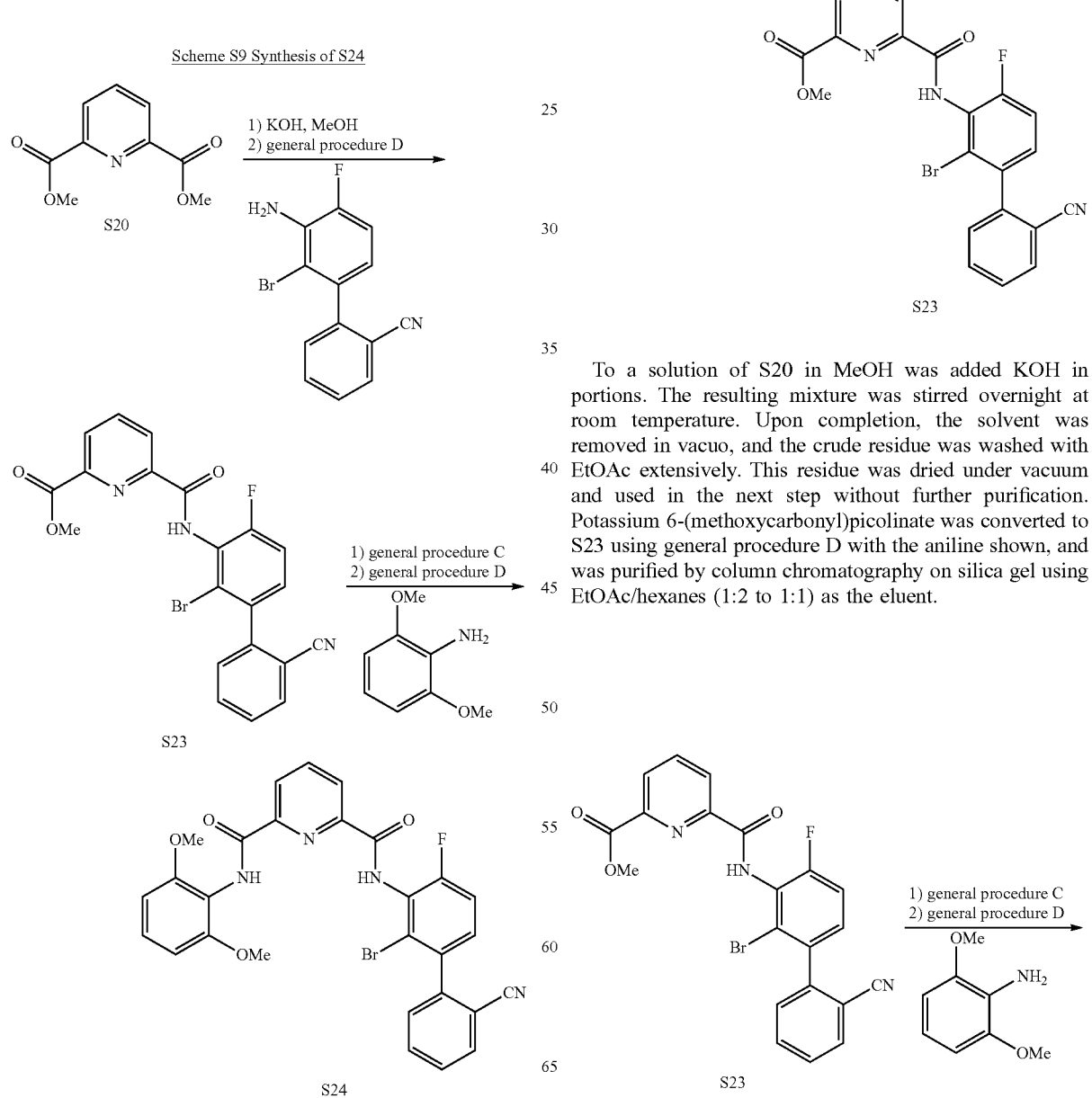

To a solution of S20 in MeOH was added KOH in portions. The resulting mixture was stirred overnight at room temperature. Upon completion, the solvent was removed in vacuo, and the crude residue was washed with EtOAc extensively. This residue was dried under vacuum and used in the next step without further purification. Potassium 6-(methoxycarbonyl)picolinate was converted to S23 using general procedure D with the aniline shown, and was purified by column chromatography on silica gel using EtOAc/hexanes (1:2 to 1:1) as the eluent.

-continued

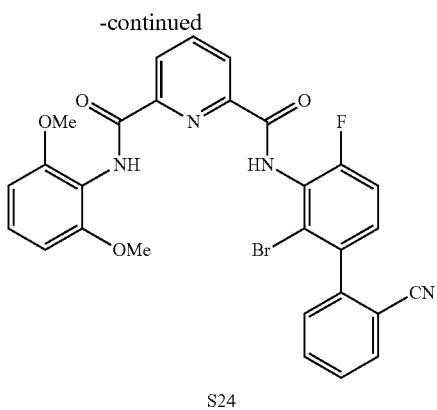

S24

S23 was converted to S24 using general procedure C and D (using 2,6-dimethoxyaniline) and was purified by column chromatography on silica gel using EtOAc/hexanes (1:1) as the eluent.

Scheme S10 Synthesis of T11

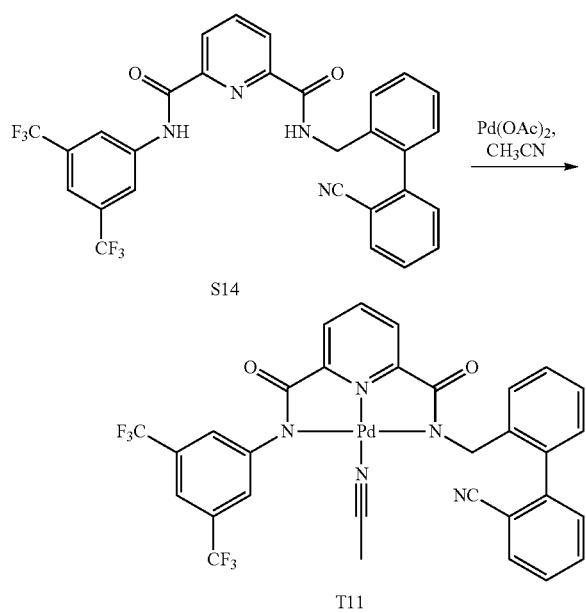

In the air, S14 (0.188 g, 0.33 mmol) and Pd(OAc)$_2$ (67.4 mg, 0.3 mmol) were added to a flask equipped with a stir bar. Acetonitrile (10 mL) was added to this flask and the resulting mixture was stirred at 60° C. Upon completion, solvent was removed in vacuo. The residue was purified by column chromatography on silica gel using DCM/MeOH (100:1 to 20:1) as the eluent giving the pure T11. (T12-T19 were synthesized following the same procedure.)

DOCUMENTS CITED IN EXAMPLES

1. Ye, M. et al. Ligand-promoted C3-selective arylation of pyridines with Pd catalysts: gram-scale synthesis of (±)-Preclamol. *J. Am. Chem. Soc.* 133, 19090-19093 (2011).
2. Kudo, N., Perseghini, M. & Fu, G. C. A versatile method for Suzuki cross-coupling reactions of nitrogen heterocycles. *Angew. Chem. Int. Ed.* 45, 1282-1284 (2006).
3. Gran, U., Wennerstrom, O. & Westman, G. Stereoselective reductions with macrocyclic NADH models. *Tetrahedron: Asymmetry* 11, 3027-3040 (2000).
4. Rudolf, S., Goebel, W. & Neumann, W. Reactions of pyridine-3-sulfonyl chloride with amines. *Acta Chim. Acad. Sci. Hung.* 64, 267-271 (1970).
5. Thelemann, J. et al. Aryl bis-sulfonamide inhibitors of IspF from *Arabidopsis thaliana* and *Plasmodium falciparum*. *ChemMedChem* 10, 2090-2098 (2015).
6. Planas, O., Whiteoak, C. J., Company, A. & Ribas, X. Regioselective access to sultam motifs through cobalt-catalyzed annulation of aryl sulfonamides and alkynes using an 8-aminoquinoline directing group. *Adv. Synth. Catal.* 357, 4003-4012 (2015).
7. Royo, E., Betancort, J. M., Davis, T. J., Carroll, P. & Walsh, P. J. Synthesis, structure, and catalytic properties of bis[bis(sulfonamido)] titanium complexes. *Organometallics* 19, 4840-4851 (2000).
8. Chen, L. et al. Structure-based design of 3-carboxy-substituted 1,2,3,4-tetrahydroquinolines as inhibitors of myeloid cell leukemia-1 (Mcl-1). *Org. Biomol. Chem.* 14, 5505-5510 (2016).
9. Mcnab, H. $^{13}$C Nuclear Magnetic Resonance Spectra of Quinoxaline Derivatives. *J. Chem. Soc., Perkin Trans. 1*, 357-363 (1982).
10. Kimura, H., Torikai, K. & Ueda, I. Termal Cyclization of Nonconjugated Aryl-Yne-Carbodiimide Furnishing a Dibenzonaphthyridine Derivative. *Chem. Pharm. Bull.* 57, 393-396 (2009).
11. Thansandote, P., Hulcoop, D. G., Langer, M. & Lautens, M. Palladium-Catalyzed Annulation of Haloanilines and Halobenzamides Using Norbornadiene as an Acetylene
12. Synthon: A Route to Functionalized Indolines, Isoquinolinones, and Indoles. *J. Org. Chem.* 74, 1673-1678 (2009).

All patents and publications referred to herein are incorporated by reference herein to the same extent as if each individual publication was specifically and individually indicated to be incorporated by reference in its entirety.

What is claimed is:
1. A palladium-coordinating template compound for directing alkenylation of a heteroaryl, the template compound of formula (II)

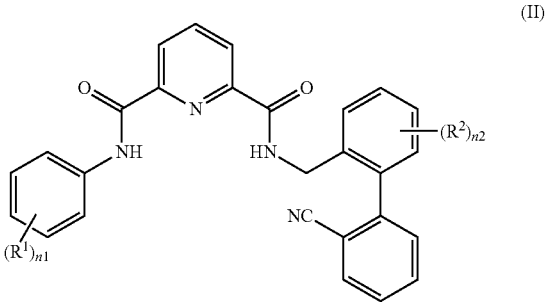

(II)

wherein
each independently selected $R^1$ is halo, trifluoromethyl, (C1-C4)alkyl, or (C1-C4)alkoxy, and n1 is 0, 1, 2, or 3; and,
each independently selected $R^2$ is halo, trifluoromethyl, (C1-C4)alkyl, or (C1-C4)alkoxy, and n1 is 0, 1, 2, or 3.

2. A template palladium complex of formula (III), for directing alkenylation of a heteroaryl, comprising the template compound of formula (II), an atom of Pd(II), and a molecule of acetonitrile,

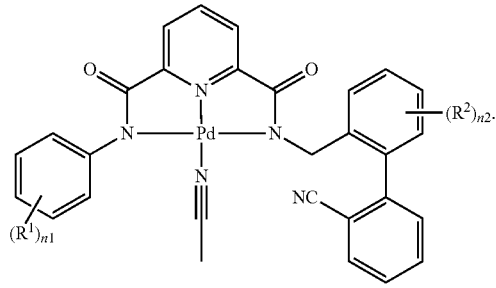

(III)

wherein $R^1$, $R^2$, n1, and n2, are as defined in claim 1.

3. The template palladium complex of claim 2, wherein $R^1$ is independently selected trifluoromethyl, t-butyl, or methoxy, or wherein $R^2$ is independently selected fluoro, ethyl, or t-butyl, or any combination thereof.

4. A method of preparing the template palladium complex of claim 2, comprising contacting the template compound of formula (II), a Pd(II) compound, and acetonitrile.

5. A method of carrying out an alkenylation of a compound comprising a quinoline group having a hydrogen atom disposed on the 5-position thereof, comprising contacting the compound comprising the quinoline group and an acrylate ester having at least one β-hydrogen, in the presence of a pre-assembled template palladium complex of formula (III) of claim 2, an N-acylaminoacid, a Pd(II) salt, an Ag(I) salt, and a Cu(II) salt, in a solvent milieu comprising 1,1,1,3,3,3-hexafluoro-2-propanol (HFIP).

6. The method of claim 5, wherein the N-acylaminoacid is N-acetylglycine.

7. The method of claim 5 wherein the Pd(II) salt is Pd(OAc)$_2$, the Ag(I) salt is AgBF$_4$, the Cu(II) salt is Cu(OAc)$_2$; and wherein the method is carried out in the presence of air or oxygen; or any combination thereof.

8. The method of claim 5 wherein the acrylate alkyl ester is ethyl acrylate.

9. The method of claim 5 wherein compound comprising a quinoline group having a hydrogen atom disposed on the 5-position thereof has further hydrogen substitution on other positions of the quinoline, and the alkenylation reaction is selective for the 5-position of the quinoline.

10. The method of claim 5, wherein the pre-assembled palladium-coordinated form of the template compound is any one of formula T15

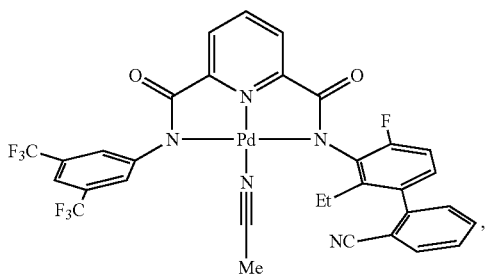

(T15)

or T16

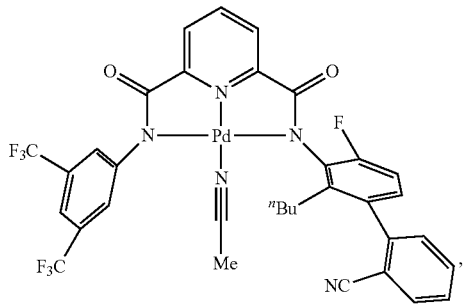

(T16)

or T17

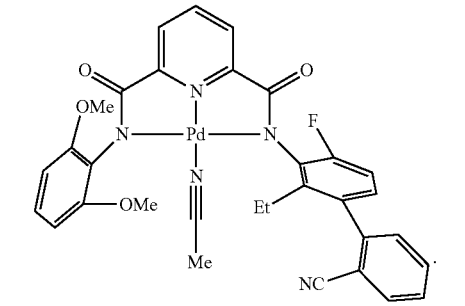

(T17)

T18

(T18)

* * * * *